United States Patent

Michihata

(10) Patent No.: US 10,548,465 B2
(45) Date of Patent: Feb. 4, 2020

(54) MEDICAL IMAGING APPARATUS AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 15/893,815

(22) Filed: Feb. 12, 2018

(65) Prior Publication Data

US 2018/0242827 A1 Aug. 30, 2018

(30) Foreign Application Priority Data

Feb. 24, 2017 (JP) ................ 2017-033933

(51) Int. Cl.
*A61B 1/00* (2006.01)
*A61B 1/045* (2006.01)
(Continued)

(52) U.S. Cl.
CPC .......... *A61B 1/045* (2013.01); *A61B 1/00006* (2013.01); *A61B 1/00009* (2013.01); *A61B 1/00045* (2013.01); *A61B 1/00186* (2013.01); *G06T 5/003* (2013.01); *G06T 5/40* (2013.01); *G06T 7/0012* (2013.01); *G06T 7/13* (2017.01); *H04N 5/2256* (2013.01); *H04N 5/2351* (2013.01); *H04N 5/2355* (2013.01);
(Continued)

(58) Field of Classification Search
CPC . A61B 1/045; A61B 1/00009; A61B 1/00186; A61B 1/00006; A61B 1/00045; G06T 7/13; G06T 5/40; G06T 5/003; G06T 7/0012; H04N 2005/2255; H04N 7/183; H04N 5/2351; H04N 5/2355; H04N 9/04511; H04N 9/04551; H04N 5/35554; H04N 7/18; H04N 5/2256
See application file for complete search history.

(56) References Cited

U.S. PATENT DOCUMENTS

2004/0263645 A1* 12/2004 Okada ................. H04N 5/3452
348/231.99
2017/0071455 A1* 3/2017 Shimamoto ........ A61B 1/00006
(Continued)

FOREIGN PATENT DOCUMENTS

JP 2014-12037 1/2014

*Primary Examiner* — Howard D Brown, Jr.
(74) *Attorney, Agent, or Firm* — Oblon, McClelland, Maier & Neustadt, L.L.P.

(57) ABSTRACT

A medical imaging apparatus includes: an imaging unit; a mode setting unit; and an imaging controller configured to drive the imaging unit in accordance with a driving mode set with the mode setting unit. The first driving mode sets exposure time of all pixels to an equal time, and outputs each of pixel signals as a pixel signal of one pixel. The second driving mode divides all the pixels into groups, setting at least one of all the pixels included in the group to have an exposure time different from an exposure time of the other pixels, and outputting, for each of the groups, an addition pixel signal as a pixel signal of one pixel. The third driving mode sets exposure time of all the pixels to an equal time, and outputs, for each of the groups, an addition pixel signal as a pixel signal of one pixel.

8 Claims, 19 Drawing Sheets

(51) Int. Cl.
*H04N 7/18* (2006.01)
*G06T 7/13* (2017.01)
*G06T 7/00* (2017.01)
*G06T 5/00* (2006.01)
*H04N 5/225* (2006.01)
*G06T 5/40* (2006.01)
*H04N 5/235* (2006.01)
*H04N 5/355* (2011.01)
*H04N 9/04* (2006.01)

(52) U.S. Cl.
CPC .......... *H04N 5/35554* (2013.01); *H04N 7/18* (2013.01); *H04N 9/04511* (2018.08); *H04N 9/04551* (2018.08); *H04N 7/183* (2013.01); *H04N 2005/2255* (2013.01)

(56) References Cited

U.S. PATENT DOCUMENTS

2018/0191973 A1\* 7/2018 Hirota .................. H04N 5/3559
2018/0227476 A1\* 8/2018 Kobayashi ......... A61B 1/00009

\* cited by examiner

MEDICAL IMAGING APPARATUS AND MEDICAL OBSERVATION SYSTEM

CROSS-REFERENCE TO RELATED APPLICATION

The present application claims priority to and incorporates by reference the entire contents of Japanese Patent Application No. 2017-033933 filed in Japan on Feb. 24, 2017.

BACKGROUND

The present disclosure relates to a medical imaging apparatus used in the medical field and that images a subject such as a human, and a medical observation system including the medical imaging apparatus.

In the related art, a medical observation system is known in the medical field. The medical observation system images the inside of a subject (inside of the living body), such as a human, to observe the inside of the living body (for example, see Japanese Unexamined Patent Publication No. 2014-12037).

The medical observation system (endoscope apparatus) disclosed in Patent Literature 1 includes an inserting unit inserted into the living body, to image the inside of the living body and output an image signal, a main member unit processing the image signal and generating a video signal for display, and a display unit displaying an endoscopic image based on the video signal.

SUMMARY

Endoscopic images may be images in which bright portions form blown-out highlights, an image in which dark portions form blocked-up shadows, or an image in which a forceps or white gauze enters the subject and the whole image is brightened. When such an image is obtained, the doctor or the like is prevented from observing the region to be actually observed. Specifically, this causes a problem in that an endoscopic image suitable for observation cannot be displayed, and improvement in convenience is prevented.

For this reason, the system may be equipped with a plurality of imaging elements having different sensitivities, to solve the problem described above. However, equipping the system with a plurality of imaging elements causes a problem in that the structure thereof is complicated.

A medical imaging apparatus according to one aspect of the present disclosure may include: an imaging unit including a plurality of pixels arranged in a matrix; a mode setting unit configured to set a driving mode of the imaging unit to one of at least two modes of a first driving mode, a second driving mode, and a third driving mode; and an imaging controller configured to drive the imaging unit in accordance with the driving mode set with the mode setting unit, wherein the first driving mode is a driving mode that sets exposure time of all the pixels in the imaging unit to an equal time, and outputs each of pixel signals of the respective pixels of all the pixels as a pixel signal of one pixel, the second driving mode is a driving mode that divides all the pixels into a plurality of groups, each of which is formed of a plurality of adjacent pixels in all the pixels, setting at least one of all the pixels included in the group to have an exposure time different from an exposure time of the other pixels, and outputting, for each of the groups, an addition pixel signal obtained by adding pixel signals of all the pixels included in the group, as a pixel signal of one pixel, and the third driving mode is a driving mode that sets exposure time of all the pixels to an equal time, and outputs, for each of the groups, an addition pixel signal obtained by adding pixel signals of all the pixels in the group, as a pixel signal of one pixel.

DETAILED DESCRIPTION

Figure 1:
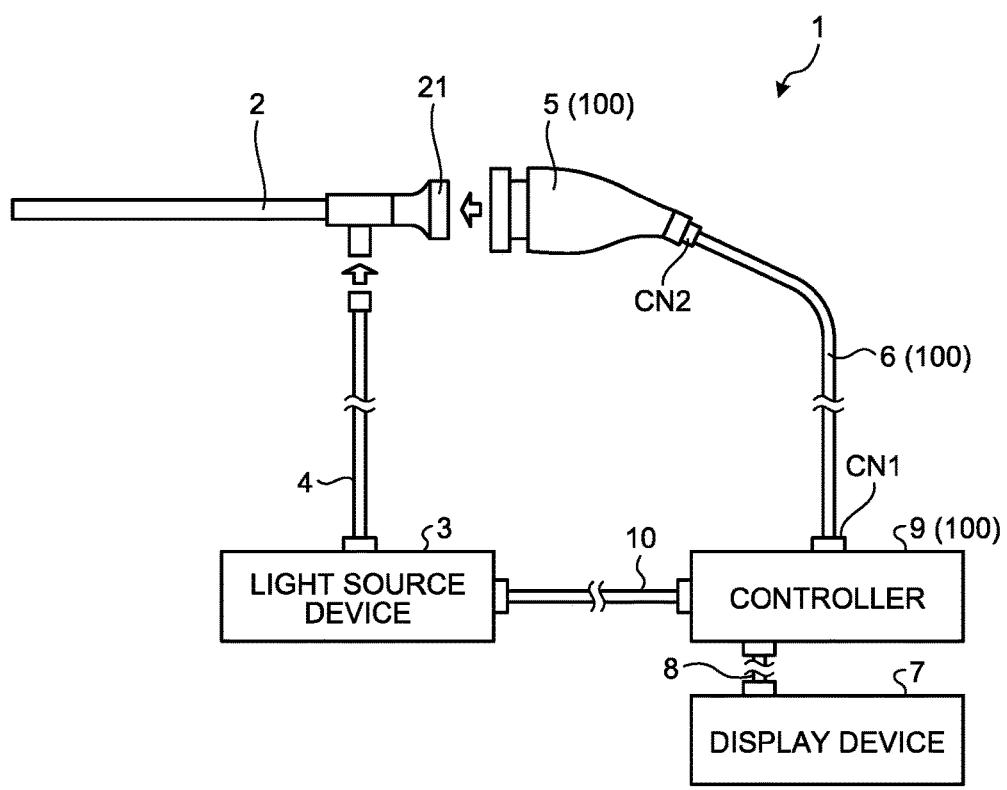
FIG. 1 is a diagram illustrating a schematic structure of a medical observation system according to a first embodiment.

The following is explanation of embodiments for carrying out the present disclosure (hereinafter referred to as "embodiments"), with reference to drawings. The present disclosure is not limited to the embodiments described hereinafter. In the drawings, the same constituent elements are denoted by the same reference numerals.

First Embodiment

Schematic Structure of Medical Observation System

FIG. 1 is a diagram illustrating a schematic structure of a medical observation system 1 according to a first embodiment.

The medical observation system 1 is an apparatus used in the medical field, to observe the subject, such as the inside of the living body. As illustrated in FIG. 1, the medical observation system 1 includes an inserting unit 2, a light source device 3, a light guide 4, a camera head 5, a first transmission cable 6, a display device 7, a second transmission cable 8, a controller 9, and a third transmission cable 10.

The inserting unit 2 is formed of a rigid endoscope. Specifically, the inserting unit 2 is rigid, or at least part thereof is flexible. The inserting unit 2 has an elongated shape, and is inserted into the living body. An optical system is provided inside the inserting unit 2. The optical system is formed of one or a plurality of lenses, and condenses a subject image.

The light source device 3 is connected with one end of the light guide 4. The light source device 3 supplies light to illuminate the inside of the living body to the end of the light guide 4, under the control of the controller 9.

The light guide 4 is detachably connected at one end with the light source device 3, and detachably connected at the other end with the inserting unit 2. The light guide 4 transmits light supplied from the light source device 3 from one end to the other end thereof, to supply the light to the inserting unit 2. The light supplied to the inserting unit 2 is emitted from a distal end of the inserting unit 2, and applied to the inside of the living body. The light (subject image) applied to the inside of the living body is condensed with the optical system in the inserting unit 2.

The camera head 5 is detachably connected with a proximal end (eyepiece portion 21 (FIG. 1)) of the inserting unit 2. The camera head 5 images a subject image condensed in the inserting unit 2, under the control of the controller 9, and outputs an image signal (RAW signal) obtained by the imaging. The image signal is, for example, an image signal of 4K or more.

The detailed structure of the camera head 5 will be described later.

The first transmission cable 6 is detachably connected at one end with the controller 9 through a connector CN1 (FIG. 1), and detachably connected at the other end with the camera head 5 through a connector CN2 (FIG. 1). The first transmission cable 6 transmits an image signal output from the camera head 5 to the controller 9, and transmits a control signal, a synchronization signal, a clock, and electric power and the like output from the controller 9 to the camera head 5.

Transmission of an image signal from the camera head 5 to the controller 9 through the first transmission cable 6 may be achieved by transmitting the image signal as an optical signal, or as an electrical signal. The same is applicable to transmission of a control signal, a synchronization signal, and a clock from the controller 9 to the camera head 5 through the first transmission cable 6.

The display device 7 is formed using a display using liquid crystal or organic electroluminescence (EL), and displays an image based on a video signal processed in the controller 9.

The second transmission cable 8 is detachably at one end with the display device 7, and detachably at the other end with the controller 9. The second transmission cable 8 transmits the video signal processed in the controller 9 to the display device 7.

The controller 9 includes a central processing unit (CPU) or the like, and generally controls operations of the light source device 3, the camera head 5, and the display device 7.

The detailed structure of the controller 9 will be described later.

The third transmission cable 10 is detachably connected at one end with the light source device 3, and detachably connected at the other end with the controller 9. The third transmission cable 10 transmits a control signal from the controller 9 to the light source device 3.

Configuration of Camera Head

The following is explanation of a configuration of the camera head 5.

Figure 2:
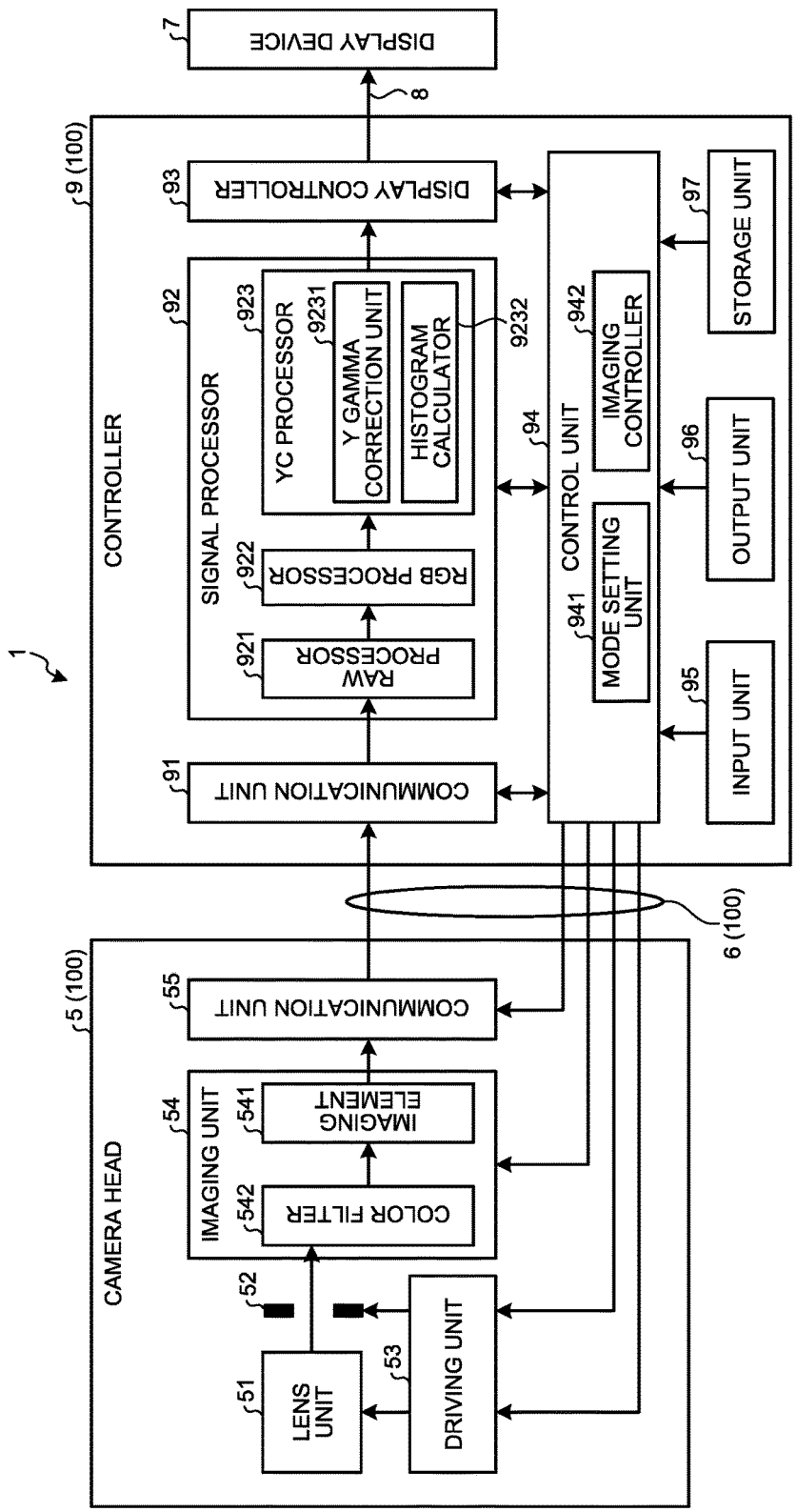
FIG. 2 is a block diagram illustrating a configuration of a camera head and a controller.

FIG. 2 is a block diagram illustrating a configuration of the camera head 5 and the controller 9.

FIG. 2 illustrates neither the connectors CN1 and CN2 between the first transmission cable 6 and the controller 9 and the camera head 5, nor the connectors between the second transmission cable 8 and the controller 9 and the display device 7, for convenience sake of explanation.

As illustrated in FIG. 2, the camera head 5 includes a lens unit 51, an iris 52, a driving unit 53, an imaging unit 54, and a communication unit 55.

The lens unit 51 is formed using one or a plurality of lenses movable along an optical axis, and forms a subject image condensed in the inserting unit 2 on an imaging surface of the imaging unit 54 (imaging element 541). The lens unit 51 is also provided with an optical zoom mechanism (not illustrated) moving one or a plurality of lenses to change the angle of view, and a focus mechanism (not illustrated) changing the focus.

The iris 52 limits an incident quantity of light condensed with the lens unit 51, to regulate the exposure.

The driving unit 53 operates the optical zoom mechanism and the focus mechanism described above, under the control of the controller 9, to change the angle of view and the focus of the lens unit 51. The driving unit 53 also drives the iris 52, under the control of the controller 9, to regulate the light quantity of the light made incident on the imaging unit 54.

Figure 3A:
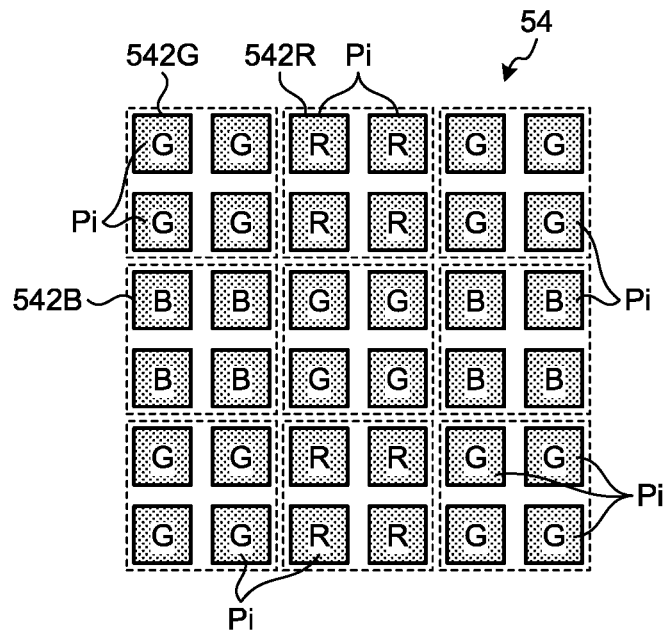
FIG. 3A is a diagram schematically illustrating an arrangement state of pixels of an imaging element, and explaining a normal mode.
Figure 3B:
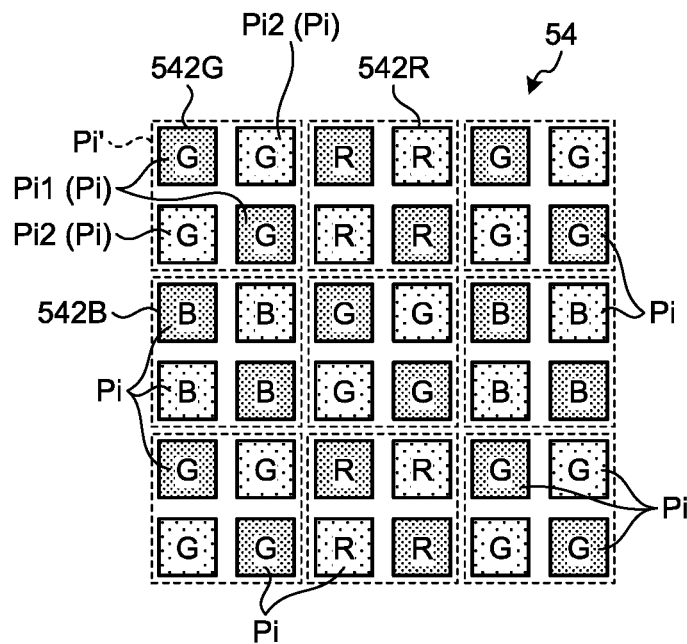
FIG. 3B is a diagram schematically illustrating an arrangement state of pixels of the imaging element, and explaining a HDR mode.
Figure 3C:
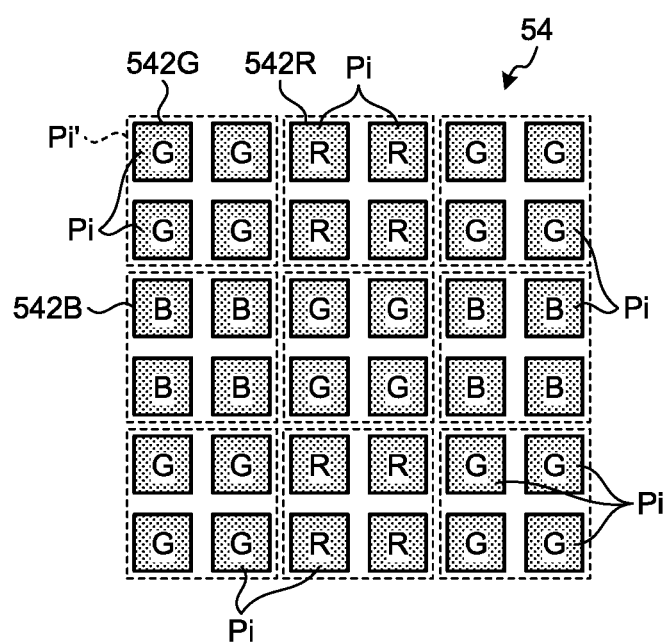
FIG. 3C is a diagram schematically illustrating an arrangement state of pixels of an imaging element, and explaining a high-sensitivity mode.

FIG. 3A to FIG. 3C are diagrams schematically illustrating an arrangement state of pixels Pi of the imaging element 541. Specifically, FIG. 3A is a diagram explaining a normal mode. FIG. 3B is a diagram explaining a HDR mode. FIG. 3C is a diagram explaining a high-sensitivity mode.

The imaging unit 54 is driven in one of the driving modes of the normal mode, the HDR mode, and the high-sensitivity mode, under the control of the controller 9, to image the inside of the living body. The imaging unit 54 is formed using a sensor chip obtained by combining an imaging element 541 (FIG. 2), such as a complementary metal oxide semiconductor (CMOS), receiving the subject image condensed in the inserting unit 2 and formed with the lens unit 51 and converting the subject image into an electrical signal, with a signal processor (not illustrated) performing signal processing (such as A/D conversion) on the electrical signal (analog signal) from the imaging element 541 and outputting an image signal, as one unitary piece. The imaging unit 54 outputs the A/D converted image signal (digital signal). The signal processor (not illustrated) described above is not always combined with the imaging element 541 as one unitary piece, but may be formed separately.

The imaging surface (light receiving surface) of the imaging element 541 is provided with a color filter 542 (FIG. 2) in which three filters are arranged in a predetermined form. The three filters are divided into groups according to the wavelength band of the light (R (red), G (green), and B (blue)) to be transmitted.

More specifically, as illustrated in FIG. 3A to FIG. 3C, the color filter 542 includes an R filter 542R transmitting light of an R wavelength band, a B filter 542B transmitting light of a B wavelength band, and a G filter 542G transmitting light of a G wavelength band. In FIG. 3A to FIG. 3C, the letter "R" is attached to each of the pixels Pi provided with the R filter 542R, the letter "G" is attached to each of the pixels Pi provided with the G filter 542G, and the letter "B" is attached to each of the pixels Pi provided with the B filter 542B.

Specifically, the image signal generated in the imaging unit 54 includes component information (pixel signal) of one of R, G, and B corresponding to the R, G, and B filters 542R, 542G, and 542B, respectively, for each of the pixels Pi.

In the first embodiment, as illustrated with broken lines in FIG. 3A to FIG. 3C, all the pixels of the imaging element 541 are divided into a plurality of groups, each of which is formed of four adjacent pixels Pi (four pixels Pi including two pixels Pi in each of the columns and including two pixels Pi in each of the rows). The R, G, and B filters 542R, 542G, and 542B are arranged in a Bayer array, when the four pixels Pi included in a group have the same filter and the group (four pixels Pi) is regarded as one pixel.

The following is an explanation of the normal mode, the HDR mode, and the high-sensitivity mode, with reference to FIG. 3A to FIG. 3C. In FIG. 3A to FIG. 3C, the depth of the color of each pixel Pi expresses the exposure time (intervals of the electronic shutter) of the pixel Pi (the paler the color is, the shorter the exposure time is).

In the case of the normal mode, the exposure time of all the pixels of the imaging element 541 is set to the equal time (for example, 1/60 [seconds] when the frame rate is 60 fps), as illustrated in FIG. 3A. The imaging unit 54 outputs each of the pixel signals output from the respective pixels Pi, as pixel signal of one pixel. Specifically, the normal mode corresponds to the driving mode normally driving the imaging unit 54, and corresponds to the first driving mode according to the present disclosure.

In the case of the HDR mode, in all the pixels of the imaging element 541, at least one pixel Pi of the four pixels Pi included in each one of the groups is set to have an exposure time different from the exposure time of the other pixels Pi. More specifically, in all the pixels of the imaging element 541, the exposure time of two pixels Pi1 positioned diagonally in the four pixels Pi included in each one of the groups is set to the equal time (for example, 1/60 [seconds] when the frame rate is 60 fps), as illustrated in FIG. 3B. In addition, in all the pixels of the imaging element 541, the exposure time of the other two pixels Pi2 positioned diagonally in the four pixels Pi included in each one of the groups is set to the equal time (for example, 1/120 [seconds] when the frame rate is 60 fps) and shorter than the exposure time of the pixels Pi1. The imaging unit 54 outputs, for each of the groups, an addition pixel signal obtained by adding the pixel signals of the four pixels Pi1 and Pi2 included in the group, as a pixel signal of one pixel Pi' (FIG. 3B). Specifically, the HDR mode is a driving mode capable of increasing the sensitivity in the case of a low incident light quantity, decreasing the sensitivity in the case of a high incident light quantity, and achieving a wide dynamic range, by adding pixel signals of the four pixels Pi1 and Pi2 included in a group and having different exposure times, and corresponds to the second driving mode according to the present disclosure.

In the case of the high-sensitivity mode, as illustrated in FIG. 3C, the exposure time of all the pixels of the imaging element 541 is set to the equal time (for example, 1/60 [seconds] when the frame rate is 60 fps). In addition, the imaging unit 54 outputs, for each of the groups, an addition pixel signal obtained by adding the pixel signals of the four pixels Pi included in the group, as a pixel signal of one pixel Pi' (FIG. 3C). Specifically, the high-sensitivity mode is a driving mode capable of increasing the sensitivity in the case of a low incident light quantity, by adding the pixel signals of the four pixels Pi included in a group and having the equal exposure time to increase the signal level per pixel Pi', and corresponds to the third driving mode according to the present disclosure.

The communication unit 55 functions as a transmitter transmitting an image signal output from the imaging unit 54 to the controller 9 through the first transmission cable 6. For example, the communication unit 55 is formed of a high-speed serial interface performing communication of an image signal with the controller 9 through the first transmission cable 6, at a transmission rate of 1 Gbps or more.

Configuration of Controller

The following is explanation of the configuration of the controller 9, with reference to FIG. 2.

As illustrated in FIG. 2, the controller 9 includes a communication unit 91, a signal processor 92, a display controller 93, a control unit 94, an input unit 95, an output unit 96, and a storage unit 97.

The communication unit 91 functions as a receiver receiving an image signal output from the camera head 5 (communication unit 55) through the first transmission cable 6. For example, the communication unit 91 is formed of a high-speed serial interface performing communication of an image signal with the communication unit 55, at a transmission rate of 1 Gbps or more.

The signal processor 92 processes the image signal (RAW signal) output from the camera head 5 (communication unit 55) and received by the communication unit 91, under the control of the control unit 94. As illustrated in FIG. 2, the signal processor 92 includes a RAW processor 921, an RGB processor 922, and a YC processor 923.

The RAW processor 921 performs RAW processing, such as demosaic processing, on the image signal (RAW signal) received by the communication unit 91, to convert the RAW signal (image signal) to an RGB signal (image signal).

The RGB processor 922 performs RGB processing, such as white balance, RGB gamma correction, and YC conversion (converting the RGB signal into a luminance signal and a color difference signal (Y, $C_B/C_R$ signals), on the image signal (RGB signal) having been subjected to RAW processing in the RAW processor 921.

The YC processor 923 processes the image signal (Y, $C_B/C_R$ signals) having been subjected to RGB processing in the RGB processor 922. As illustrated in FIG. 2, the YC processor 923 includes a Y gamma correction unit 9231 and a histogram calculator 9232.

The Y gamma correction unit 9231 performs Y gamma correction on the luminance signal (Y signal) included in the image signal (Y, $C_B/C_R$ signals) having been subjected to RGB processing in the RGB processor 922. A Y gamma curve in the Y gamma correction is changed according to the driving mode of the imaging unit 54 set in the control unit 94. Specifically, the Y gamma curve in the Y gamma correction differs between the case in which the driving mode of the imaging unit 54 is set to the normal mode, the case in which the driving mode is set to the HDR mode, and the case in which the driving mode is set to the high-sensitivity mode.

The histogram calculator 9232 calculates a histogram of the luminance signal (Y signal) for each pixel based on the luminance signal (Y signal) included in the image signal (Y, $C_B/C_R$ signals) having been subjected to RGB processing in the RGB processor 922.

The display controller 93 generates a display video signal from the luminance signal (Y signal) having been subjected to Y gamma correction in the Y gamma correction unit 9231, and the color difference signal ($C_B/C_R$ signal) included in the image signal (Y, $C_B/C_R$ signals) having been subjected to RGB processing in the RGB processor 922. The display controller 93 outputs the video signal to the display device 7, through the second transmission cable 8.

The control unit 94 is formed of, for example, a CPU. The control unit 94 outputs a control signal through the first and the third transmission cables 6 and 10, to control operations of the light source device 3 and the camera head 5, and control the operations of the whole controller 9. As illustrated in FIG. 2, the control unit 94 includes a mode setting unit 941, and an imaging controller 942.

The mode setting unit 941 sets the driving mode of the imaging unit 54 to one of the normal mode, the HDR mode, and the high-sensitivity mode based on the histogram calculated in the histogram calculator 9232.

The imaging controller 942 outputs a control signal to the imaging unit 54 through the first transmission cable 6, and drives the imaging unit 54 in the driving mode set with the mode setting unit 941.

The input unit 95 is formed using an operating device, such as a mouse, a key board, and a touch panel, and receives user's operations.

The output unit 96 is formed using a speaker and a printer, and the like, to output various types of information.

The storage unit 97 stores a program executed with the control unit 94, and information necessary for processing with the control unit 94.

The camera head 5, the first transmission cable 6, and the controller 9 described above have a function as a medical imaging apparatus 100 (FIG. 1 and FIG. 2) according to the present disclosure.

Operations of Controller

The following is explanation of operations of the controller 9 described above.

Figure 4:
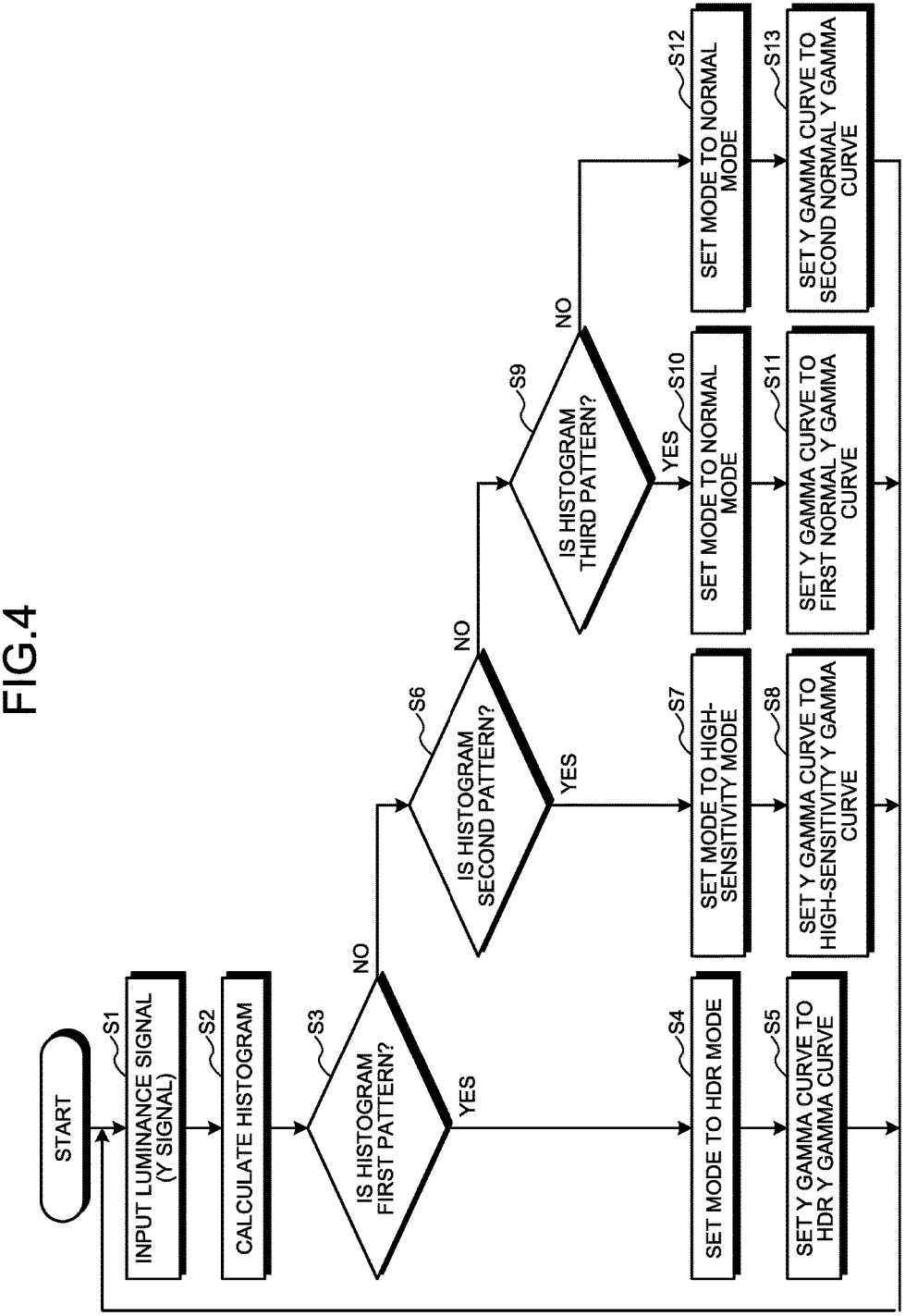
FIG. 4 is a flowchart illustrating operations of the controller.

FIG. 4 is a flowchart illustrating operations of the controller 9.

The following explanation mainly illustrates operations of the YC processor 923, the mode setting unit 941, and the imaging controller 942.

First, the histogram calculator 9232 receives a luminance signal (Y signal) included in the image signal (Y, $C_B/C_R$ signals) having been subjected to RGB processing in the RGB processor 922 (Step S1), and calculates a histogram of the luminance signal (Y signal) for each pixel (Step S2).

After Step S2, the mode setting unit 941 determines whether the histogram calculated at Step S2 is a histogram of a first pattern (Step S3).

Figure 5A:
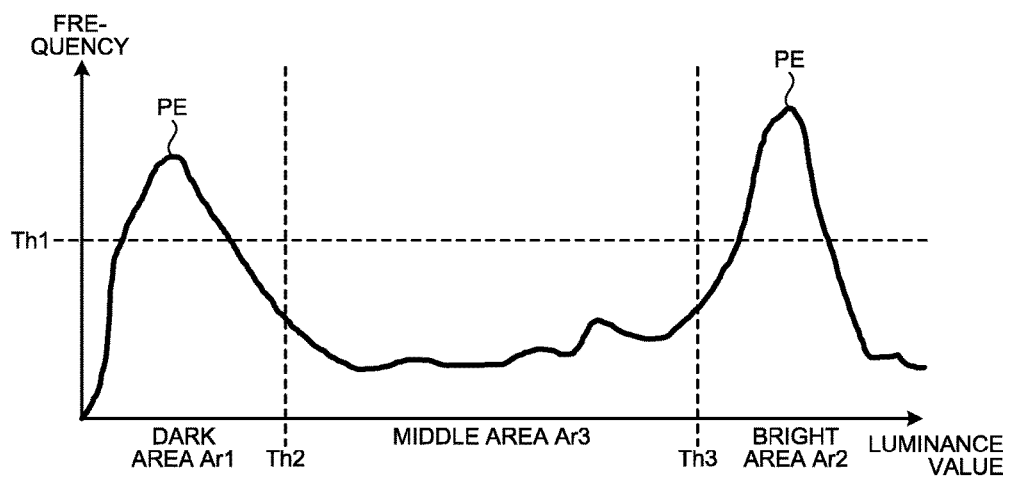
FIG. 5A is a diagram illustrating an example of a histogram serving as a first pattern.

FIG. 5A is a diagram illustrating an example of a histogram of the first pattern.

In FIG. 5A, a peak with a frequency exceeding a first threshold Th1 is referred to as peak PE. In addition, the area with a luminance value equal to or lower than a second threshold th2 is referred to as dark area Ar1, the area with a luminance value equal to or higher than a third threshold Th3 higher than the second threshold Th2 is referred to as bright area Ar2, and the area between the dark area An and the bright area Ar2 is referred to as middle area Ar3. The same is applicable to FIG. 6A, FIG. 7A, and FIG. 8A.

For example, the histogram of the first pattern includes at least two peaks PE, as illustrated in FIG. 5A. The at least two peaks PE are located in the dark area Ar1 and the bright area Ar2.

Specifically, at Step S3, the mode setting unit 941 detects the three peaks PE in the order of high frequency from the histogram calculated at Step S2. In addition, the mode setting unit 941 determines whether at least two peaks PE in the detected three peaks PE are located in the dark area An and the bright area Ar2. In this manner, the mode setting unit 941 determines whether the histogram calculated at Step S2 is a histogram of the first pattern.

When it is determined that the histogram is a histogram of the first pattern (Yes at Step S3), the mode setting unit 941 sets the driving mode of the imaging unit 54 to the HDR mode (Step S4). Thereafter, the imaging controller 942 outputs a control signal to the imaging unit 54 through the first transmission cable 6, to drive the imaging unit 54 in the HDR mode.

After Step S4, the control unit 94 sets the Y gamma curve in Y gamma correction to an HDR Y gamma curve (Step S5). Thereafter, the Y gamma correction unit 9231 performs Y gamma correction on the luminance signal (Y signal) included in the image signal (Y, $C_B/C_R$ signals) having been subjected to RGB processing in the RGB processor 922, with the HDR Y gamma curve. After Step S5, the controller 9 returns to Step S1.

Figure 5B:
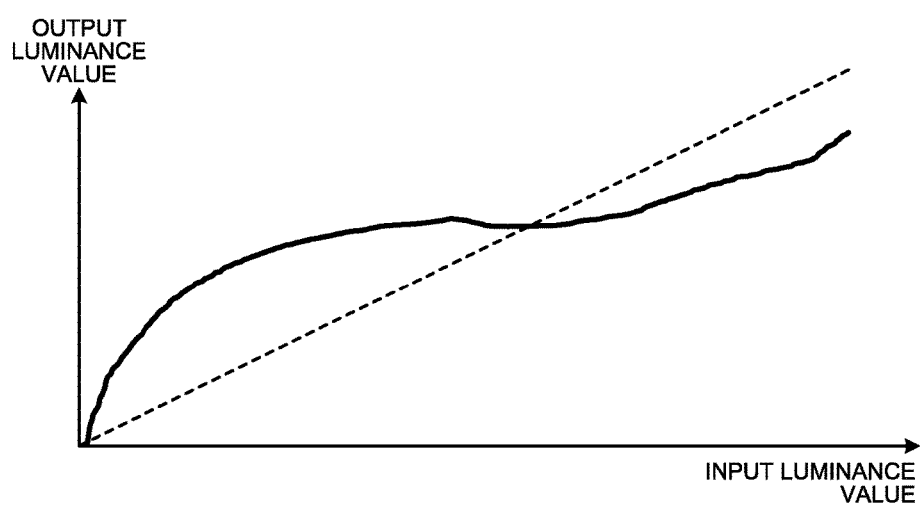
FIG. 5B is a diagram illustrating an example of a HDR Y gamma curve.

FIG. 5B is a diagram illustrating an example of the HDR Y gamma curve.

For example, as illustrated in FIG. 5B, the HDR Y gamma curve is a gamma curve to correct the luminance value to a higher value for a pixel with a low luminance value in the input luminance signal (Y signal), and correct the luminance value to a lower value for a pixel with a high luminance value.

When it is determined that the histogram is not a histogram of the first pattern (No at Step S3), the mode setting unit 941 determines whether the histogram calculated at Step S2 is a histogram of a second pattern (Step S6).

Figure 6A:
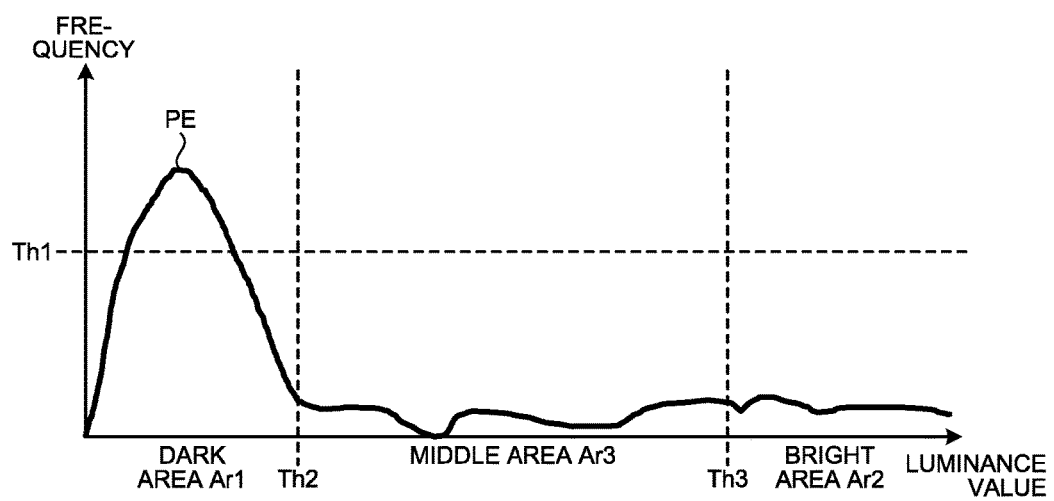
FIG. 6A is a diagram illustrating an example of a histogram serving as a second pattern.

FIG. 6A is a diagram illustrating an example of a histogram of the second pattern.

For example, as illustrated in FIG. 6A, the histogram of the second pattern includes at least one peak PE. In addition, the at least one peak PE is not located in the bright area Ar2, but located in the dark area Ar1.

Specifically, at Step S6, the mode setting unit 941 detects three peaks PE in the order of high frequency from the histogram calculated at Step S2. Thereafter, the mode setting unit 941 determines whether none of the detected three peaks PE is located in the bright area Ar2, and at least one peak PE of the detected three peaks PE is located in the dark area Ar1. In this manner, the mode setting unit 941 determines whether the histogram calculated at Step S2 is a histogram of the second pattern.

When it is determined that the histogram is a histogram of the second pattern (Yes at Step S6), the mode setting unit 941 sets the driving mode of the imaging unit 54 to the high-sensitivity mode (Step S7). Thereafter, the imaging controller 942 outputs a control signal to the imaging unit 54 through the first transmission cable 6, to drive the imaging unit 54 in the high-sensitivity mode.

After Step S7, the control unit 94 sets the Y gamma curve in Y gamma correction to a high-sensitivity Y gamma curve (Step S8). Thereafter, the Y gamma correction unit 9231 performs Y gamma correction on the luminance signal (Y signal) included in the image signal (Y, $C_B/C_R$ signals) having been subjected to RGB processing in the RGB processor 922, with the high-sensitivity Y gamma curve. After Step S8, the controller 9 returns to Step S1.

Figure 6B:
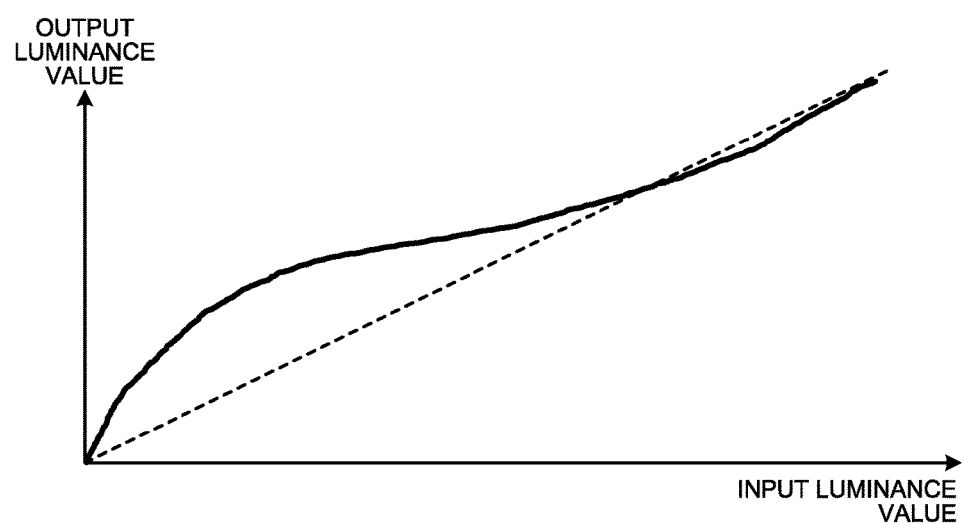
FIG. 6B is a diagram illustrating an example of a high-sensitivity Y gamma curve.

FIG. 6B is a diagram illustrating an example of the high-sensitivity Y gamma curve.

For example, as illustrated in FIG. 6B, the high-sensitivity Y gamma curve is a gamma curve to perform no correction on the luminance value for a pixel with a high luminance value in the input luminance signal (Y signal), and correct the luminance value to a higher value for a pixel with a low luminance value.

When it is determined that the histogram is not a histogram of the second pattern (No at Step S6), the mode setting unit 941 determines whether the histogram calculated at Step S2 is a histogram of a third pattern (Step S9).

Figure 7A:
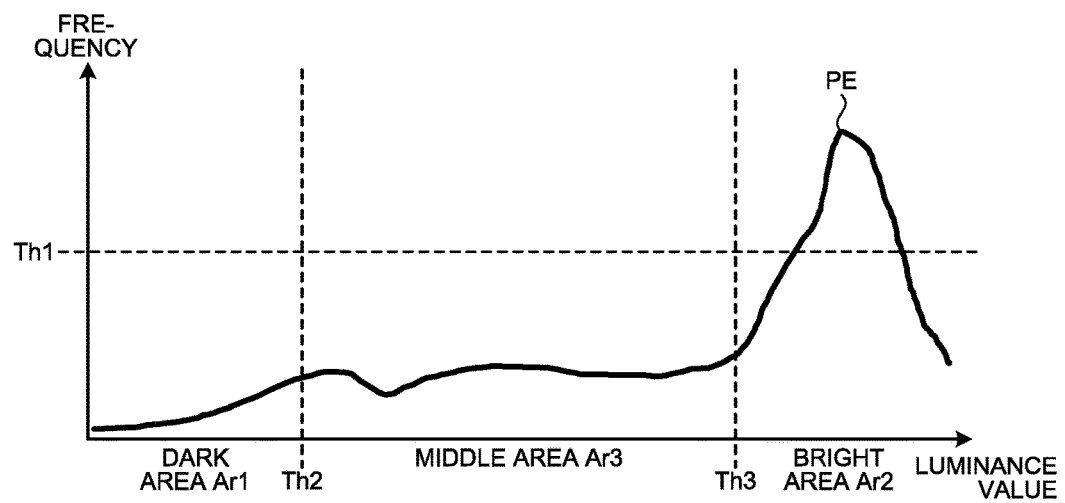
FIG. 7A is a diagram illustrating an example of a histogram serving as a third pattern.

FIG. 7A is a diagram illustrating an example of a histogram of the third pattern.

For example, as illustrated in FIG. 7A, the histogram of the third pattern includes at least one peak PE. In addition, the at least one peak PE is not located in the dark area Ar1, but located in the bright area Ar2.

Specifically, at Step S9, the mode setting unit 941 detects three peaks PE in the order of high frequency from the histogram calculated at Step S2. Thereafter, the mode setting unit 941 determines whether none of the detected three peaks PE is located in the dark area Ar1, and at least one peak PE of the detected three peaks PE is located in the bright area Ar2. In this manner, the mode setting unit 941 determines whether the histogram calculated at Step S2 is a histogram of the third pattern.

When it is determined that the histogram is a histogram of the third pattern (Yes at Step S9), the mode setting unit 941 sets the driving mode of the imaging unit 54 to the normal mode (Step S10). Thereafter, the imaging controller 942 outputs a control signal to the imaging unit 54 through the first transmission cable 6, to drive the imaging unit 54 in the normal mode.

After Step S10, the control unit 94 sets the Y gamma curve in Y gamma correction to a first normal Y gamma curve (Step S11). Thereafter, the Y gamma correction unit 9231 performs Y gamma correction on the luminance signal (Y signal) included in the image signal (Y, $C_B/C_R$ signals) having been subjected to RGB processing in the RGB processor 922, with the first normal Y gamma curve. After Step S11, the controller 9 returns to Step S1.

Figure 7B:
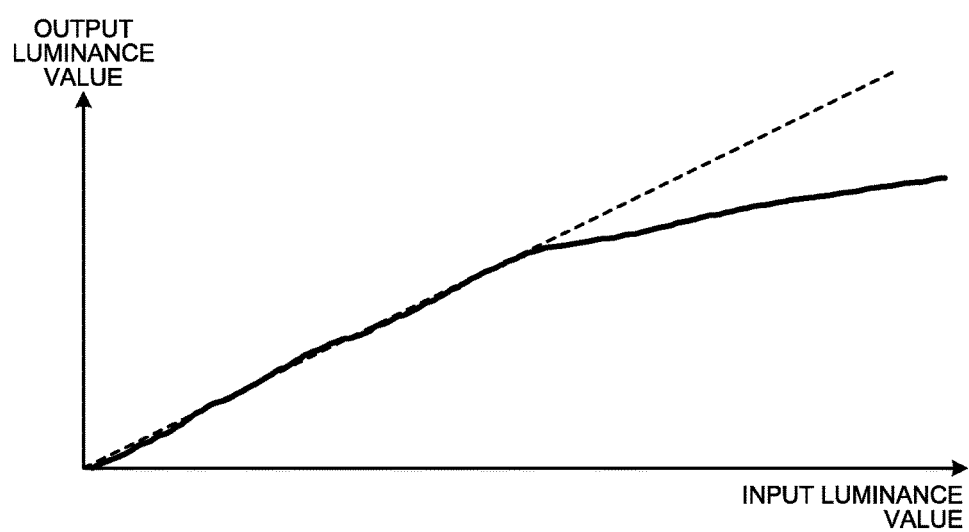
FIG. 7B is a diagram illustrating an example of a first normal Y gamma curve.

FIG. 7B is a diagram illustrating an example of the first normal Y gamma curve.

For example, as illustrated in FIG. 7B, the first normal Y gamma curve is a gamma curve to perform no correction on the luminance value for a pixel with a low luminance value in the input luminance signal (Y signal), and correct the luminance value to a lower value for a pixel with a high luminance value.

When it is determined that the histogram is not a histogram of the third pattern (No at Step S9), the mode setting unit 941 determines that the histogram calculated at Step S2 is a histogram of a fourth pattern.

Figure 8A:
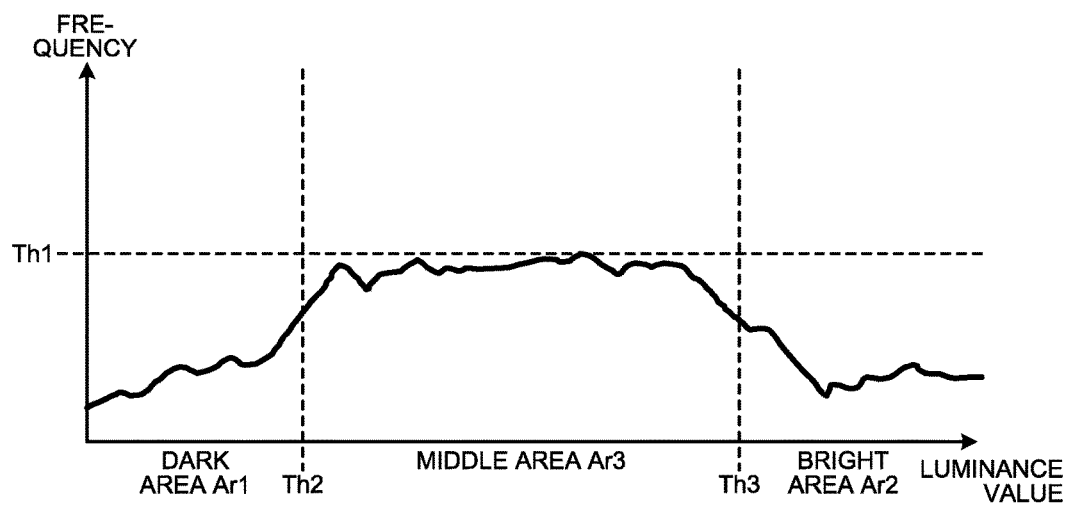
FIG. 8A is a diagram illustrating an example of a histogram serving as a fourth pattern.

FIG. 8A is a diagram illustrating an example of a histogram of the fourth pattern.

For example, as illustrated in FIG. 8A, the histogram of the fourth pattern includes no peaks PE, or, even when the histogram includes a peak PE, the peak PE is located in neither the dark area Ar1 nor the bright area Ar2.

The mode setting unit 941 sets the driving mode of the imaging unit 54 to the normal mode (Step S12). In addition, the imaging controller 942 outputs a control signal to the imaging unit 54 through the first transmission cable 6, to drive the imaging unit 54 in the normal mode.

After Step S12, the control unit 94 sets the Y gamma curve in Y gamma correction to a second normal Y gamma curve (Step S13). Thereafter, the Y gamma correction unit 9231 performs Y gamma correction on the luminance signal (Y signal) included in the image signal (Y, $C_B/C_R$ signals) having been subjected to RGB processing in the RGB processor 922, with the second normal Y gamma curve. After Step S13, the controller 9 returns to Step S1.

Figure 8B:
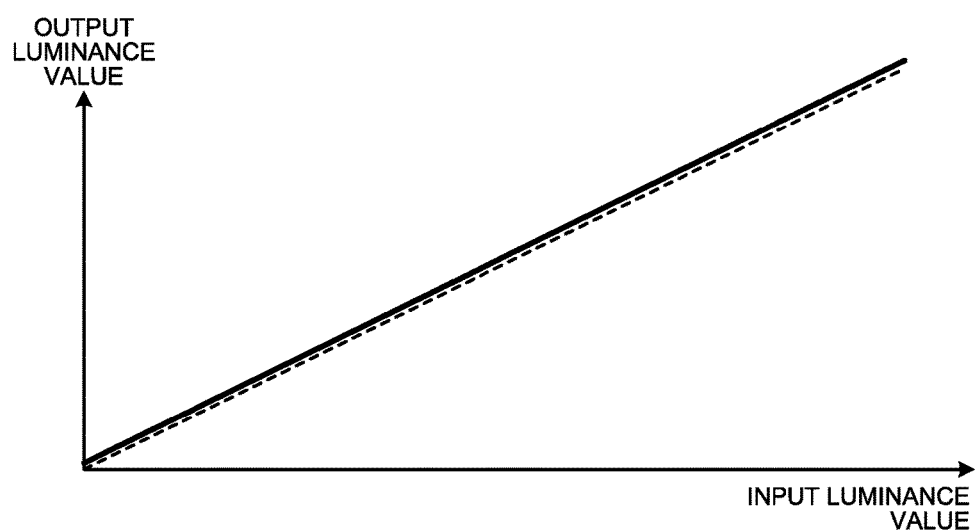
FIG. 8B is a diagram illustrating an example of a second normal Y gamma curve.

FIG. 8B is a diagram illustrating an example of the second normal Y gamma curve.

For example, as illustrated in FIG. 8B, the second normal Y gamma curve is a linear gamma curve to output the input luminance signal (Y signal) without any correction. Specifically, with the second normal Y gamma curve, the Y gamma correction unit 9231 performs no Y gamma correction on the luminance signal (Y signal).

The first embodiment described above produces the following effects.

The medical imaging apparatus 100 according to the first embodiment includes the mode setting unit 941 setting the driving mode of the imaging unit 54 to one of the normal mode, the HDR mode, and the high-sensitivity mode.

In addition, when an image suitable for observation is displayed, the driving mode of the imaging unit 54 is set to the normal mode. However, when an image (an image in which bright portions form blown-out highlights, an image in which dark portions form blocked-up shadows, or an image in which a forceps or white gauze enters the subject and the whole image is brightened) unsuitable for observation is displayed, the driving mode of the imaging unit 54 is set to the HDR mode or the high-sensitivity mode. Setting the driving mode of the imaging unit 54 as described above enables display of an image suitable for observation, and improves convenience.

Accordingly, the medical imaging apparatus 100 according to the first embodiment produces the effect of removing the necessity for providing a plurality of imaging elements having different sensitivities, and enabling improvement in convenience without complicating the structure.

In addition, in the medical imaging apparatus 100 according to the first embodiment, the mode setting unit 941 sets the driving mode of the imaging unit 54 based on a histogram of the luminance signal (Y signal) for each of the pixels.

This structure enables proper determination as to whether the image imaged with the imaging unit 54 is an image suitable for observation, and proper setting of the mode to the driving mode according to the state (histogram) of the image. For example, the mode can be set to the HDR mode, in the case of an image in which both the bright area and the dark area have high rate (FIG. 5A) as the occupying rate in the whole image. In addition, the mode can be set to the high-sensitivity mode, in the case of an image in which the dark area has high rate (FIG. 6A) as the occupying rate in the whole image.

In addition, the medical imaging apparatus 100 according to the first embodiment includes a Y gamma correction unit 9231 performing Y gamma correction on the luminance signal (Y signal) for each of the pixels in the image imaged with the imaging unit 54. The Y gamma curve in the Y gamma correction differs according to the driving mode of the imaging unit 54 (FIG. 5B, FIG. 6B, FIG. 7B, and FIG. 8B).

This structure further enhances the effect of enabling display of an image suitable for observation described above, by Y gamma correction performed together with change of the driving mode of the imaging unit 54.

Second Embodiment

The following is explanation of a second embodiment.

In the following explanation, constituent elements similar to those in the first embodiment described above are denoted by the same reference numerals, and detailed explanation thereof is omitted or simplified.

Figure 9:
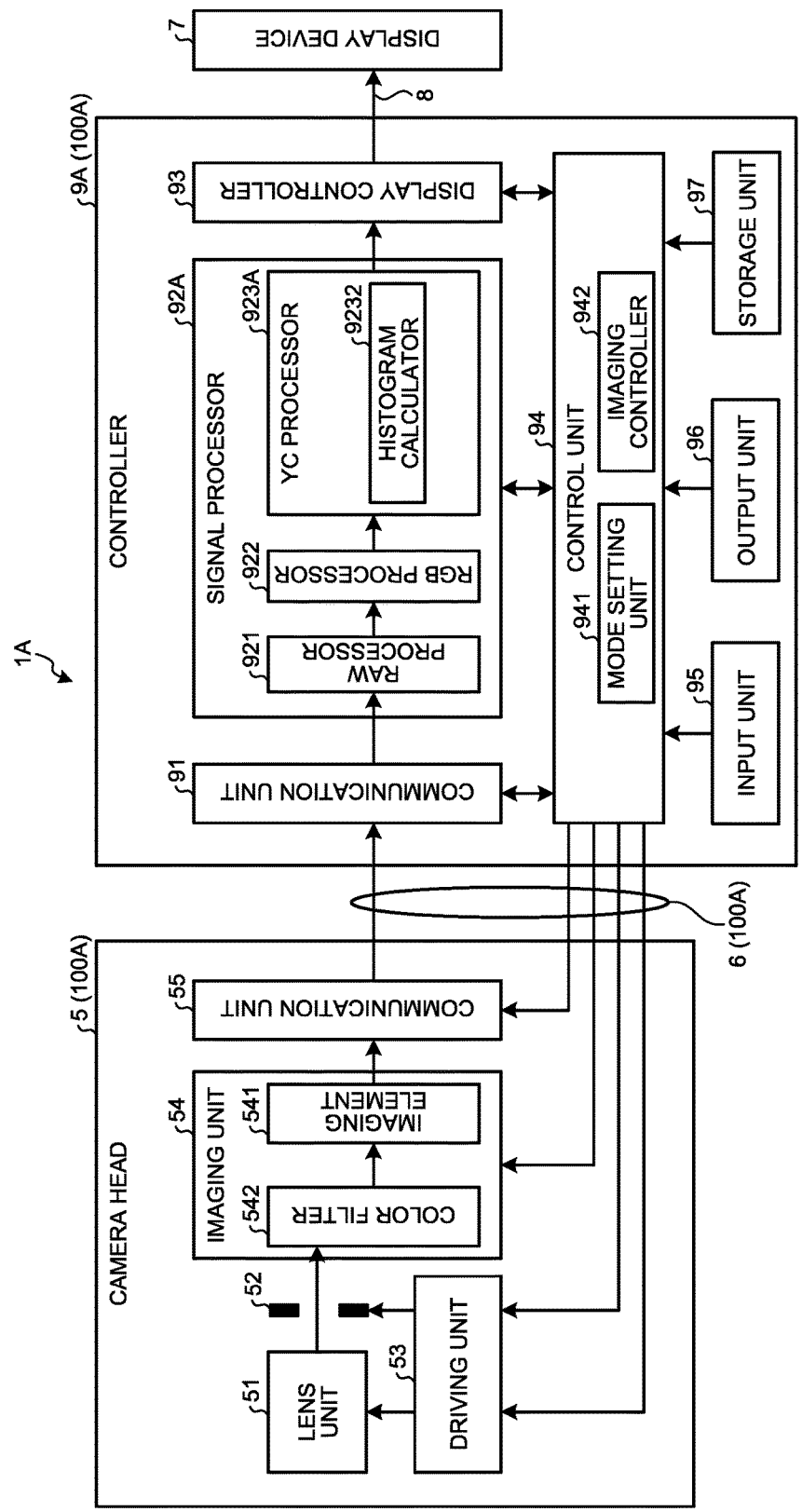
FIG. 9 is a diagram corresponding to FIG. 2, and illustrating a schematic configuration of a medical observation system according to a second embodiment.

FIG. 9 is a diagram corresponding to FIG. 2, and illustrating a schematic configuration of a medical observation system 1A according to the second embodiment.

As illustrated in FIG. 9A, the medical observation system 1A (controller 9A (signal processor 92A (YC processor 923A))) according to the second embodiment is different from the medical observation system 1 explained in the first embodiment above, only in that the Y gamma correction unit 9231 is omitted. Specifically, the medical observation system 1A according to the second embodiment performs no Y gamma correction on the luminance signal (Y signal) included in the image signal (Y, $C_B/C_R$ signals) having been subjected to RGB processing in the RGB processor 922. Specifically, in operations of the controller 9A according to the second embodiment, Steps S5, S8, S11, and S13 are omitted in the operations (FIG. 4) of the controller 9 explained in the first embodiment above. In addition, the display controller 93 according to the second embodiment generates a display video signal from the image signal (Y, $C_B/C_R$ signals) having been subjected to RGB processing in the RGB processor 922.

The camera head 5, the first transmission cable 6, and the controller 9A have a function as a medical imaging apparatus 100A (FIG. 9) according to the present disclosure.

As in the second embodiment described above, even when adopting the structure in which the Y gamma correction unit 9231 is omitted, the same effect as that of the first embodiment is produced.

Third Embodiment

The following is explanation of a third embodiment.

In the following explanation, constituent elements similar to those in the first embodiment described above are denoted by the same reference numerals, and detailed explanation thereof is omitted or simplified.

Figure 10:
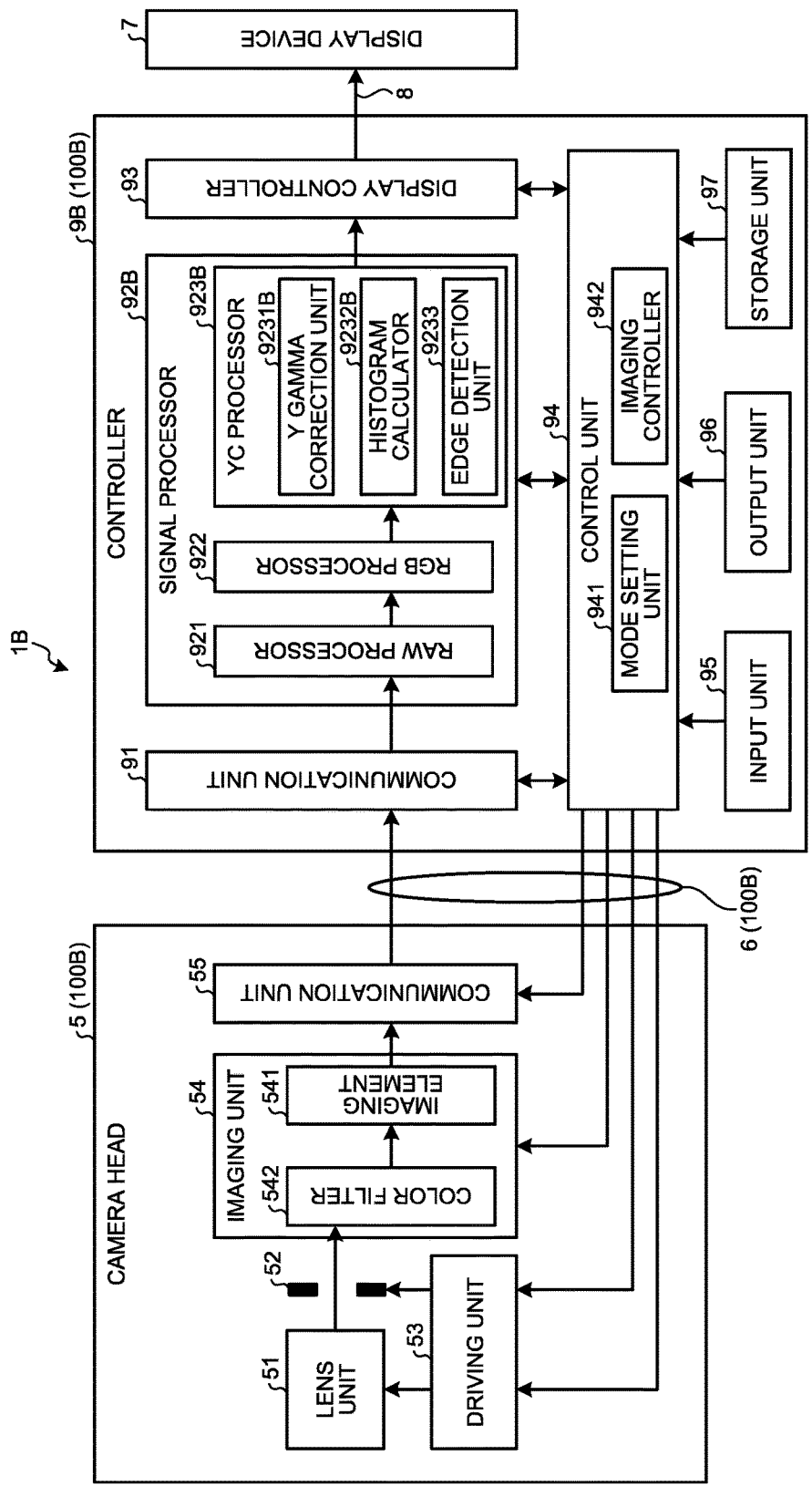
FIG. 10 is a diagram corresponding to FIG. 2, and illustrating a schematic configuration of a medical observation system according to a third embodiment.

FIG. 10 is a diagram corresponding to FIG. 2, and illustrating a schematic configuration of a medical observation system 1B according to the third embodiment.

As illustrated in FIG. 10, the medical observation system 1B (controller 9B (signal processor 92B (YC processor 923B))) according to the third embodiment has a structure obtained by adding an edge detection unit 9233 performing mask edge detection processing to the medical observation system 1 explained in the first embodiment above.

Figure 11:
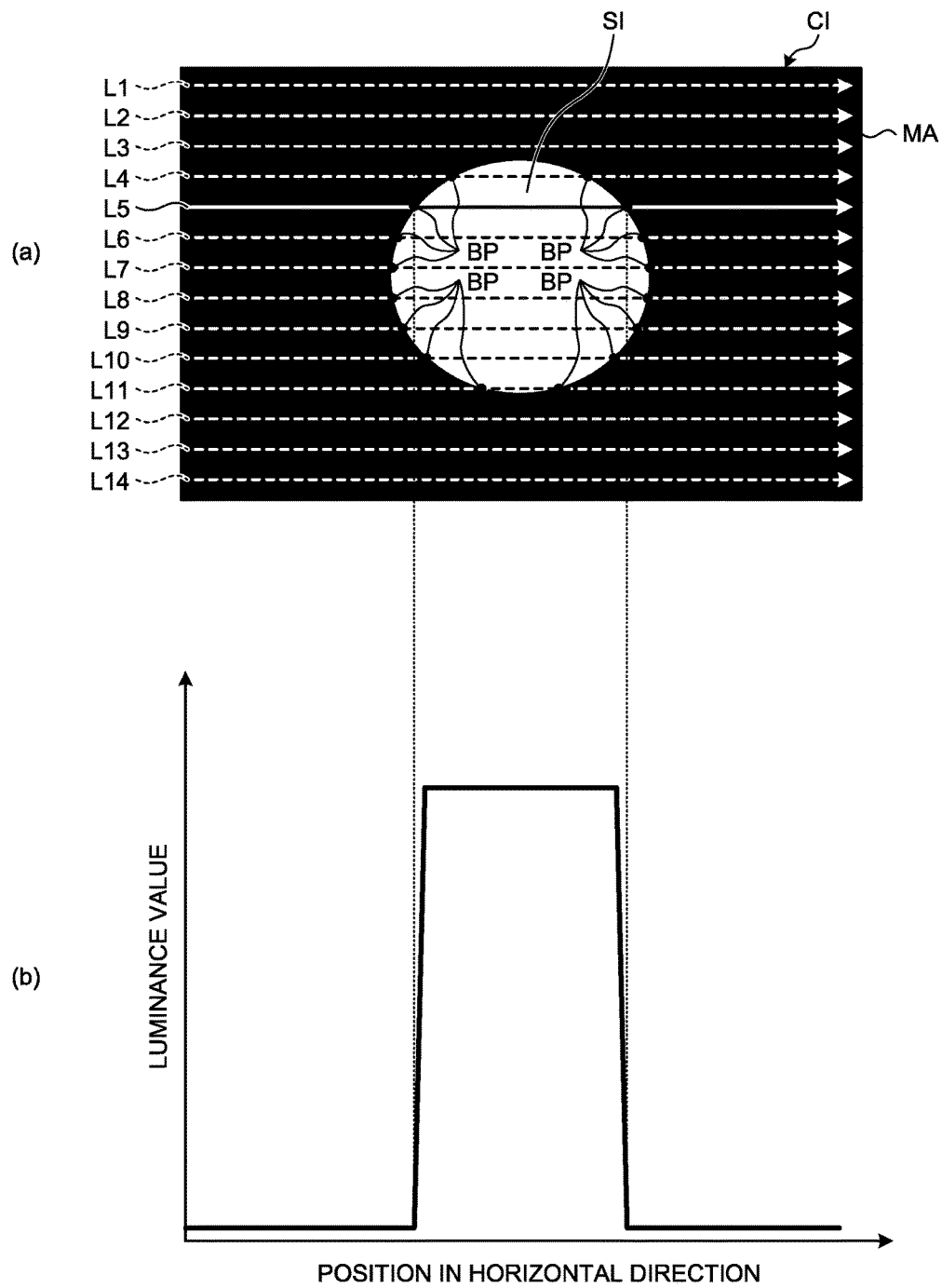
FIG. 11 is a diagram for explaining mask edge detection processing.

FIG. 11 is a diagram illustrating mask edge detection processing. Specifically, (a) of FIG. 11 is a diagram illustrating an example of a captured image CI imaged in the imaging unit 54. (b) of FIG. 11 is a diagram illustrating distribution of the luminance values at a horizontal line L5 in the captured image CI illustrated in (a) of FIG. 11.

The light (subject image) reflected inside the living body and condensed in the inserting unit 2 has a substantially circular cross section. For this reason, the subject image SI in the captured image CI imaged in the imaging unit 54 has a substantially circular shape, as illustrated in (a) of FIG. 11. Specifically, the captured image CI includes the subject image SI, and a mask area MA (the black portion in (a) of FIG. 11) other than the subject image SI.

The edge detection unit 9233 performs mask edge detection processing described later, to detect boundary points BP ((a) of FIG. 11) between the subject image SI and the mask area MA.

Specifically, as illustrated in (a) of FIG. 11, the edge detection unit 9233 detects distribution of the luminance values at each of a plurality of (14 in the third embodiment) horizontal lines L1 to L14 in the captured image CI based on the luminance signal (Y signal) included in the image signal (Y, $C_B/C_R$ signals) having been subjected to RGB processing in the RGB processor 922. In the captured image CI, the area of the subject image SI has a luminance value higher than that of the mask area MA. Specifically, for example, as illustrated in (b) of FIG. 11, the luminance distribution at the horizontal line L5 has a high luminance value between the two boundary points BP between subject image SI and the mask area MA, and has a low luminance value in the other portions. For this reason, the edge detection unit 9233 is capable of recognizing a plurality of boundary points BP between the subject image SI and the mask area MA, by detecting the distribution of the luminance values at each of the horizontal lines L1 to L14. The edge detection unit 9233 also recognizes the area of the subject image SI enclosed with the boundary points BP based on the recognized boundary points BP.

In addition, a Y gamma correction unit 9231B according to the third embodiment performs Y gamma correction only on the luminance signal (Y signal) corresponding to each of the pixels in the area of the subject image SI enclosed with boundary points BP recognized with the edge detection unit 9233, in the luminance signals (Y signals) included in the image signal (Y, $C_B/C_R$ signals) having been subjected to RGB processing in the RGB processor 922, with any Y gamma curve set with the mode setting unit 941. In addition, the Y gamma correction unit 9231B performs no Y gamma correction on the luminance signal (Y signal) corresponding to the pixels other than the pixels in the area of the subject image SI enclosed with boundary points BP recognized with the edge detection unit 9233.

Besides, a histogram calculator 9232B according to the third embodiment calculates a histogram of the luminance signal (Y signal) of each of pixels in the area of the subject image SI enclosed with boundary points BP recognized with the edge detection unit 9233, in the luminance signals (Y signals) included in the image signal (Y, $C_B/C_R$ signals) having been subjected to RGB processing in the RGB processor 922.

The camera head 5, the first transmission cable 6, and the controller 9B have a function as a medical imaging apparatus 100B (FIG. 10) according to the present disclosure.

Figure 12:
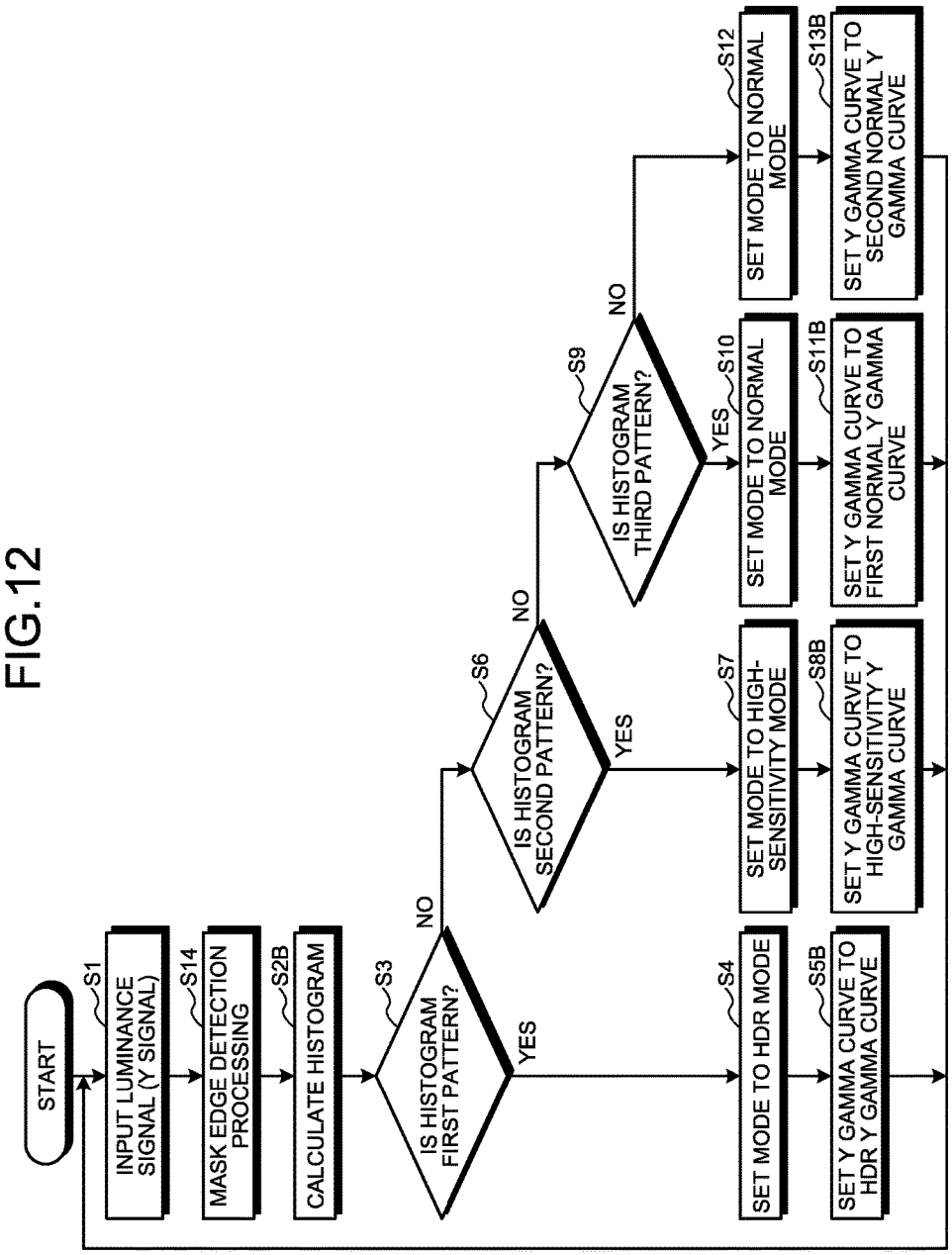
FIG. 12 is a flowchart illustrating operations of the controller.

FIG. 12 is a flowchart illustrating operations of the controller 9B.

As illustrated in FIG. 12, operations of the controller 9B according to the third embodiment are obtained by adding Step S14 to the operations (FIG. 4) of the controller 9 explained in the first embodiment above, and adopting Steps S2B, S5B, S8B, S11B, and S13B, instead of Steps S2, S5, S8, S11, and S13. For this reason, the following explanation illustrates only Steps S14, S2B, S5B, S8B, S11B, and S13B.

Step S14 is executed after Step S1.

Specifically, at Step S14, the edge detection unit 9233 performs mask edge detection processing.

After Step S14, at Step S2B, the histogram calculator 9232B calculates a histogram of the luminance signal (Y signal) of each of the pixels in the area of the subject image SI enclosed with boundary points BP recognized with the edge detection unit 9233, in the luminance signals (Y signals) included in the image signal (Y, $C_B/C_R$ signals) having been subjected to RGB processing in the RGB processor 922.

In addition, at Steps S5B, S8B, S11B, and S13B, the Y gamma correction unit 9231B performs Y gamma correction only on the luminance signal (Y signal) of each of the pixels in the area of the subject image SI enclosed with boundary points BP recognized at Step S14, in the luminance signals (Y signals) included in the image signal (Y, $C_B/C_R$ signals) having been subjected to RGB processing in the RGB processor 922, with any of the Y gamma curves.

The third embodiment described above produces the following effect, in addition to the effect similar to those of the first embodiment described above.

When Y gamma correction is performed on the luminance signal (Y signal) corresponding to the pixel in the mask area MA, the black portion in the mask area MA is not properly displayed as black portion, that is, misadjusted black level may occur, and noise may be highlighted.

The controller 9B according to the third embodiment includes the edge detection unit 9233 detecting boundary points BP between the subject image SI and the mask area MA. In addition, the Y gamma correction unit 9231B performs Y gamma correction only on the luminance signal (Y signal) corresponding to each of the pixels in the area of the subject image SI enclosed with the boundary points BP.

This structure prevents occurrence of misadjusted black level in the mask area MA, and enables proper display of the captured image CI.

In addition, when a histogram of the luminance signal (Y signal) of each of the pixels for all the pixels in the captured image CI is calculated, proper determination of the state (brightness) of the subject image SI is difficult because each of the pixels in the mask area MA serving as black portion and having low luminance value is also counted.

The controller 9B according to the third embodiment has a structure in which the histogram calculator 9232B calculates a histogram of the luminance signal (Y signal) of each pixel in the pixels in the area of the subject image SI enclosed with the boundary points BP.

Because each of the pixels in the mask area MA is not counted, this structure enables proper determination of the state (brightness) of the subject image SI. Accordingly, this structure enables setting the imaging unit 54 to the proper driving mode based on the histogram, and proper setting of the Y gamma curve.

Fourth Embodiment

The following is explanation of a fourth embodiment.

In the following explanation, constituent elements similar to those in the first embodiment described above are denoted by the same reference numerals, and detailed explanation thereof is omitted or simplified.

In the first embodiment described above, the present disclosure is applied to the medical observation system 1 using a rigid endoscope (inserting unit 2).

However, in the fourth embodiment, the prevent disclosure is applied to a medical observation system using a video scope including an imaging unit on a distal end side of the inserting unit.

Figure 13:
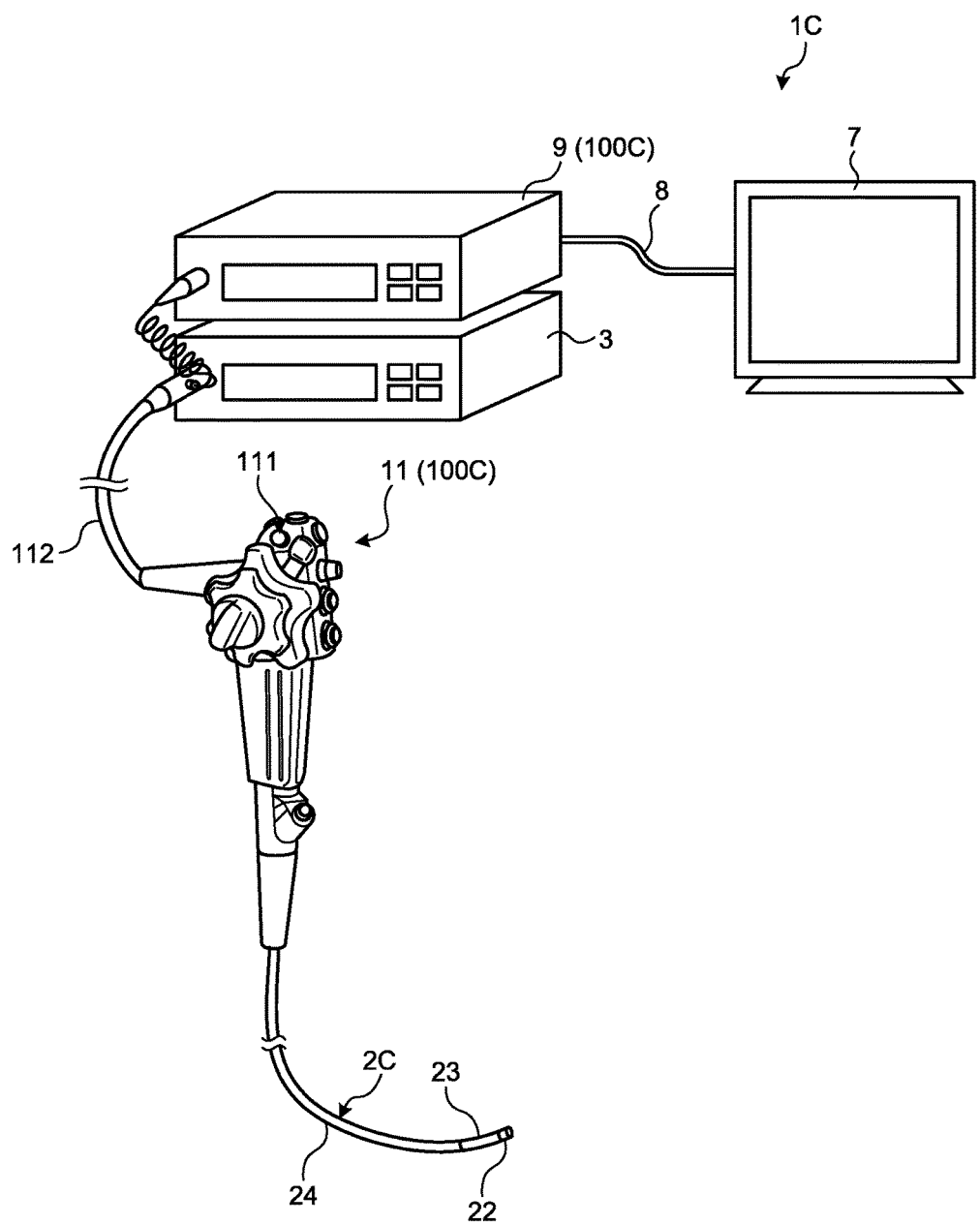
FIG. 13 is a diagram illustrating a schematic structure of a medical observation system according to a fourth embodiment.

FIG. 13 is a diagram illustrating a schematic structure of a medical observation system 1C according to the fourth embodiment.

As illustrated in FIG. 13, the medical observation system 1C according to the fourth embodiment includes an endoscope 11 inserting an inserting unit 2C into the living body, to image an internal image of the region to be observed and output an image signal, the light source device 3 generating illumination light emitted from a distal end of the endoscope 11, the controller 9 processing the image signal output from the endoscope 11, and a display device 7 connected with the controller 9 through the second transmission cable 8 and displaying an image based on the video signal processed with the controller 9.

As illustrated in FIG. 13, the endoscope 11 includes a flexible inserting unit 2C having an elongated shape, an operating unit 111 connected to a proximal end of the inserting unit 2C and receiving inputs of various types of operating signals, and a universal cord 112 extending from the operating unit 111 in a direction different from a direction in which the inserting unit 2C extends and including various types of cables connected with the light source device 3 and the controller 9.

As illustrated in FIG. 13, the inserting unit 2C includes a distal end portion 22, a bendable bending portion 23 connected with a proximal end of the distal end portion 22 and formed of a plurality of bending pieces, and a long flexible tube portion 24 connected with a proximal end portion of the bending portion 23 and having flexibility.

The inside of the distal end portion 22 includes a structure similar to that of the imaging unit 54 explained in the first embodiment above, although specific illustration thereof is omitted. In addition, the inside of the operating unit 111 includes a structure similar to that of the communication unit 55 explained in the first embodiment above, although specific illustration thereof is omitted. The image signal imaged with the distal end portion 22 (imaging unit) is output to the controller 9, through the operating unit 111 and the universal cord 112.

The endoscope 11 and the controller 9 have a function as a medical imaging apparatus 100C (FIG. 13) according to the present disclosure.

The fourth embodiment explained above also produces the effects similar to those of the first embodiment described above, even when the flexible endoscope (endoscope 11) is adopted.

The following is explanation of a fifth embodiment.

In the following explanation, constituent elements similar to those in the first embodiment described above are denoted by the same reference numerals, and detailed explanation thereof is omitted or simplified.

In the first embodiment described above, the present disclosure is applied to the medical observation system 1 using a rigid endoscope (inserting unit 2).

However, in the fifth embodiment, the prevent disclosure is applied to a medical observation system using a surgical microscope enlarging and imaging a predetermined visual field area inside the subject (inside of the living body) and the surface of the subject (surface of the living body).

Figure 14:
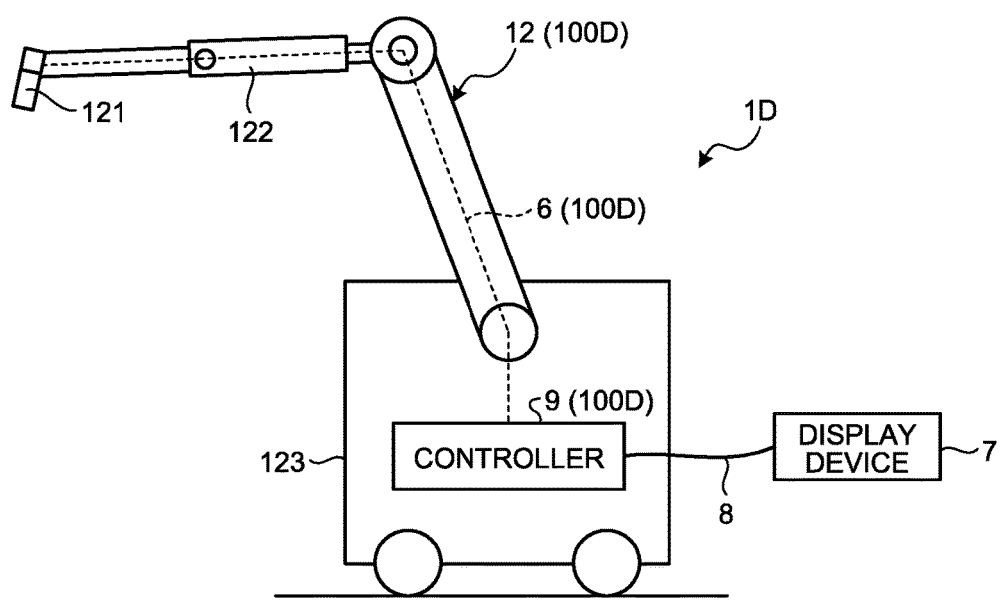
FIG. 14 is a diagram illustrating a schematic structure of a medical observation system according to a fifth embodiment.

FIG. 14 is a diagram illustrating a schematic structure of a medical observation system 1D according to the fifth embodiment.

As illustrated in FIG. 14, the medical observation system 1D according to the fifth embodiment includes a surgical microscope 12 imaging an image to observe the subject and outputting an image signal, the controller 9 processing the image signal output from the surgical microscope 12, and the display device 7 connected with the controller 9 through the second transmission cable 8 and displaying an image based on a video signal processed with the controller 9.

As illustrated in FIG. 14, the surgical microscope 12 includes a microscope portion 121 enlarging and imaging a minute region of the subject, and outputting an image signal, a support portion 122 including an arm connected with a proximal end portion of the microscope portion 121 and rotatably supporting the microscope portion 121, and a base portion 123 rotatably supporting a proximal end portion of the support portion 122 and movable on the floor surface.

The controller 9 is provided in the base portion 123, as illustrated in FIG. 14.

The base portion 123 may be configured to be fixed on the ceiling or the wall surface, to support the support portion 122, instead of being provided movably on the floor surface. The base portion 123 may include a light source portion generating illumination light applied from the surgical microscope 12 to the subject.

The microscope portion 121 includes a structure similar to those of the imaging unit 54 and the communication unit 55 explained in the first embodiment above, and specific illustration thereof is omitted. The image signal imaged with the microscope portion 121 (imaging unit) is output to the controller 9, through the first transmission cable 6 disposed along the support portion 122.

The surgical microscope 12, the first transmission cable 6, and the controller 9 have a function as a medical imaging apparatus 100D (FIG. 14) according to the present disclosure.

The fifth embodiment explained above also produces the effects similar to those of the first embodiment described above, even when the surgical microscope 12 is adopted.

Other Embodiments

The embodiments to carry out the present disclosure have been described above, but the present disclosure is not limited only to the first to the fifth embodiments described above.

Figure 15A:
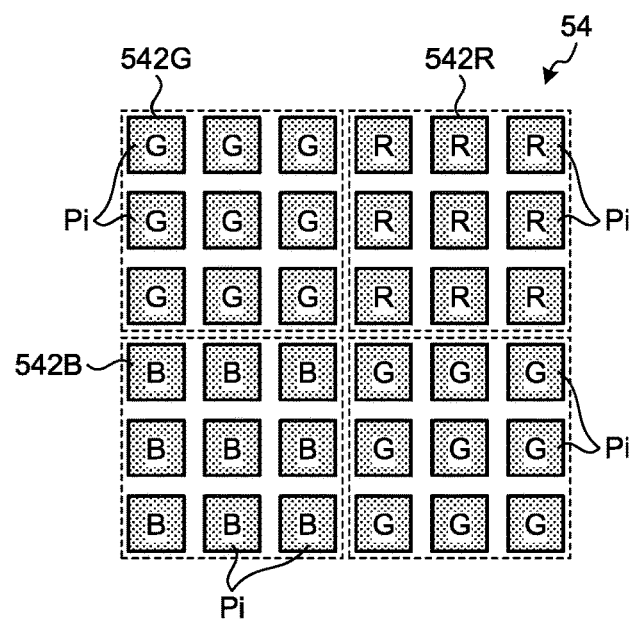
FIG. 15A is a diagram illustrating a first modification of the first to the fifth embodiments.
Figure 15B:
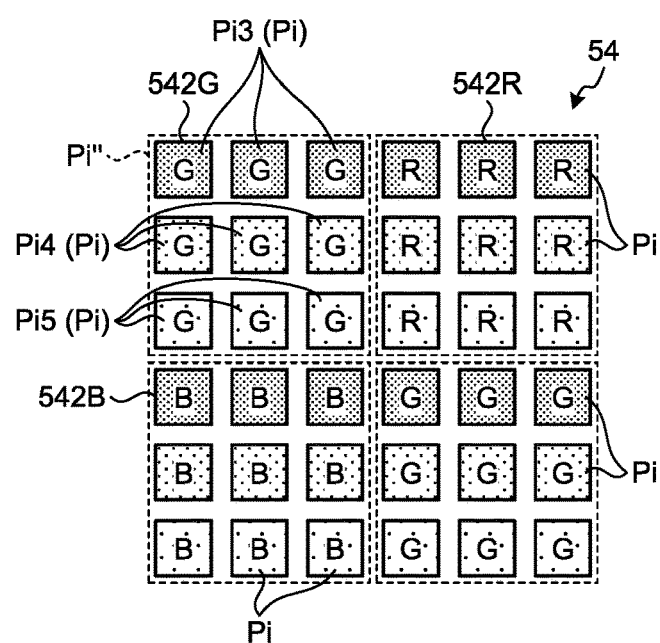
FIG. 15B is a diagram illustrating the first modification of the first to the fifth embodiments.
Figure 15C:
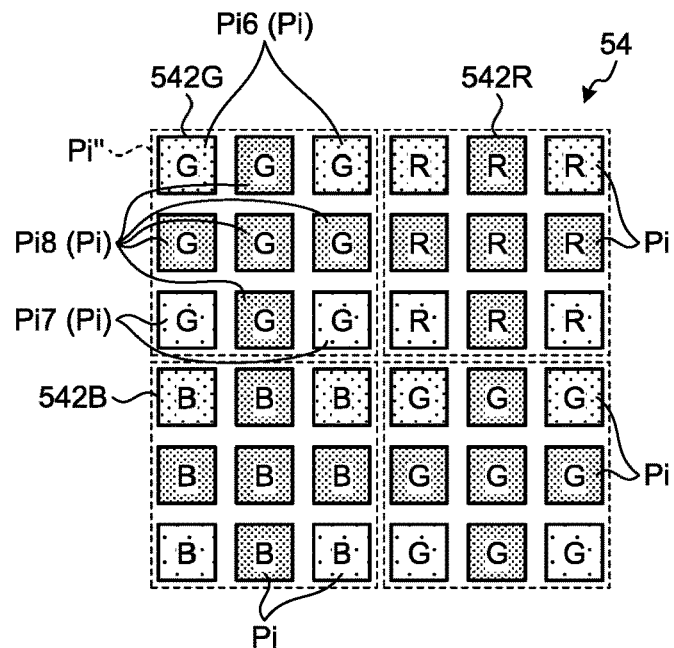
FIG. 15C is a diagram illustrating the first modification of the first to the fifth embodiments.
Figure 15D:
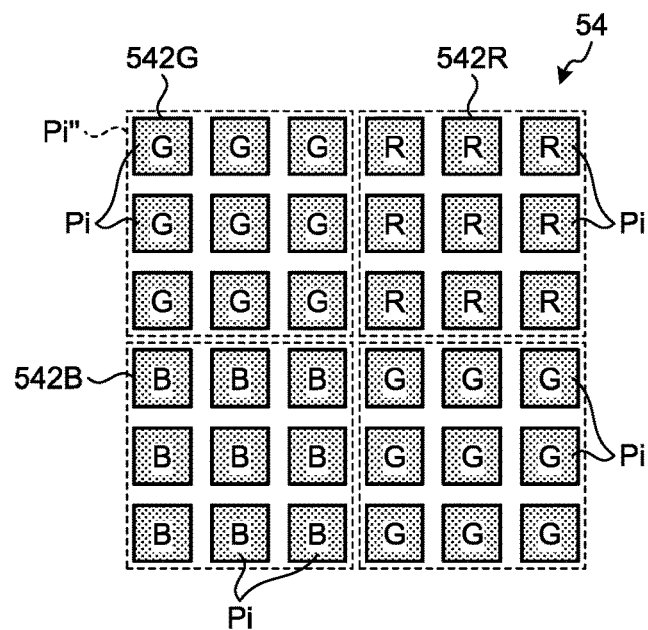
FIG. 15D is a diagram illustrating the first modification of the first to the fifth embodiments.

FIG. 15A to FIG. 15D are diagrams illustrating a first modification of the first to the fifth embodiments. Specifically, FIG. 15A is a diagram corresponding to FIG. 3A and illustrating the normal mode. FIG. 15B and FIG. 15C are diagrams corresponding to FIG. 3B and illustrating the HDR mode. FIG. 15D is a diagram corresponding to FIG. 3C and illustrating the high-sensitivity mode.

The first to the fifth embodiments described above have the structure in which all the pixels of the imaging element 541 are divided into a plurality of groups, each of which is formed of four adjacent pixels Pi, but the number of pixels Pi included in each of the groups is not limited to four, and may be another number. For example, as illustrated with broken lines in FIG. 15A to FIG. 15D, all the pixels of the imaging element 541 may be divided into a plurality of groups, each of which is formed of nine adjacent pixels Pi (nine pixels Pi including three pixels Pi in each of the columns and including three pixels Pi in each of the rows). In this state, the R, G, and B filters 542R, 542G, and 542B are arranged in a Bayer array, when the nine pixels Pi included in a group have the same filter and the group (nine pixels Pi) is regarded as one pixel, as illustrated in FIG. 15A to FIG. 15D.

The following is an explanation of the normal mode, the HDR mode, and the high-sensitivity mode in the case of the structure as described above, with reference to FIG. 15A to FIG. 15D. In FIG. 15A to FIG. 15D, the depth of the color of each pixel Pi expresses the exposure time of the pixel Pi (the paler the color is, the shorter the exposure time is), in accordance with FIG. 3A to FIG. 3C.

In the case of the normal mode, the exposure time of all the pixels of the imaging element 541 is set to the equal time (for example, 1/60 [seconds] when the frame rate is 60 fps), as illustrated in FIG. 15A. The imaging unit 54 outputs each of the pixel signals output from the respective pixels Pi, as pixel signal of one pixel.

In the case of the HDR mode illustrated in FIG. 15B, in all the pixels of the imaging element 541, the exposure time of uppermost three pixels Pi3 of the nine pixels Pi included in each one of the groups is set to the equal exposure time (for example, 1/60 [seconds] when the frame rate is 60 fps). In addition, in all the pixels of the imaging element 541, the exposure time of three pixels Pi4 adjacent to the three pixels Pi3 of the nine pixels Pi included in each one of the groups is set to be shorter than the exposure time of the pixels Pi3 and to the equal exposure time (for example, 1/120 [seconds] when the frame rate is 60 fps). Besides, in all the pixels of the imaging element 541, the exposure time of three pixels Pi5 adjacent to the three pixels Pi4 of the nine pixels Pi included in each one of the groups is set to be shorter than the exposure time of the pixels Pi4 and to the equal exposure time (for example, 1/240 [seconds] when the frame rate is 60 fps). The imaging unit 54 outputs, for each of the groups, an addition pixel signal obtained by adding the pixel signals of the nine pixels Pi3 and Pi5 included in the group, as a pixel signal of one pixel Pi″ (FIG. 15B).

In the case of the HDR mode illustrated in FIG. 15C, in all the pixels of the imaging element 541, the exposure time of five pixels Pi8, excluding pixels Pi6 and Pi7 located in four corner portions, of the nine pixels Pi included in each one of the groups is set to the equal exposure time (for example, 1/60 [seconds] when the frame rate is 60 fps). In addition, in all the pixels of the imaging element 541, the exposure time of the pixels Pi6 located in the upper corner portions in FIG. 15C in the nine pixels Pi included in each one of the groups is set to be shorter than the exposure time of the pixels Pi8 and to the equal exposure time (for example, 1/120 [seconds] when the frame rate is 60 fps). Besides, in all the pixels of the imaging element 541, the exposure time of the pixels Pi7 located in the lower corner portions in FIG. 15C in the nine pixels Pi included in each one of the groups is set to be shorter than the exposure time of the pixels Pi6 and to the equal exposure time (for example, 1/240 [seconds] when the frame rate is 60 fps). The imaging unit 54 outputs, for each of the groups, an addition pixel signal obtained by adding the pixel signals of the nine pixels Pi6 and Pi8 included in the group, as a pixel signal of one pixel Pi″ (FIG. 15C).

In the case of the high-sensitivity mode, as illustrated in FIG. 15D, the exposure time of all the pixels of the imaging element 541 is set to the equal time (for example, 1/60 [seconds] when the frame rate is 60 fps). In addition, the imaging unit 54 outputs, for each of the groups, an addition pixel signal obtained by adding the pixel signals of the nine pixels Pi included in the group, as a pixel signal of one pixel Pi' (FIG. 15D).

Figure 16:
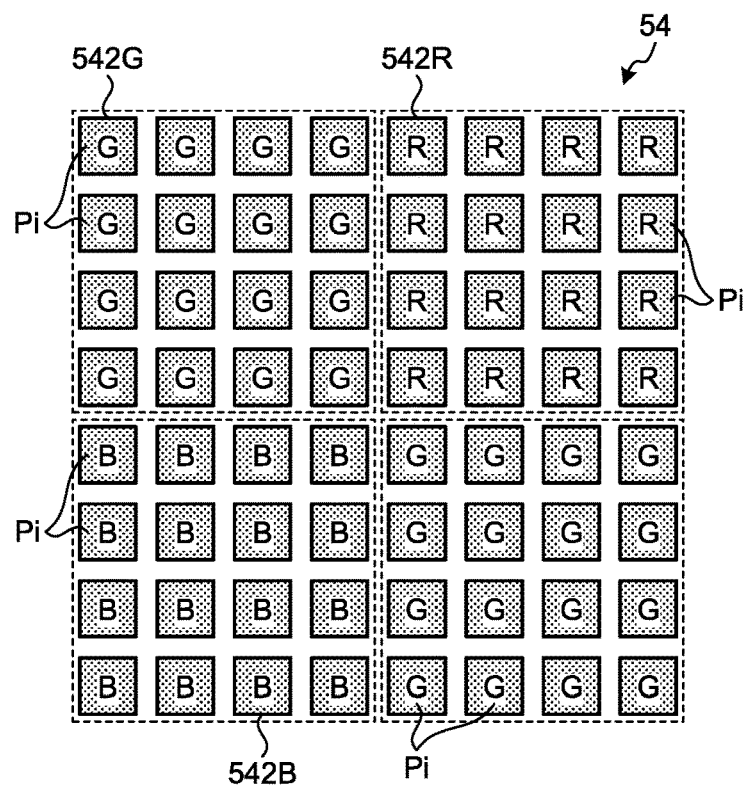
FIG. 16 is a diagram illustrating a second modification of the first to the fifth embodiments.

FIG. 16 is a diagram illustrating a second modification of the first to the fifth embodiments. Specifically, FIG. 16 is a diagram corresponding to FIG. 3A to FIG. 3C, and schematically illustrating the arrangement state of pixel Pi of the imaging element 541.

In addition, as illustrated with broken lines in FIG. 16, all the pixels of the imaging element 541 may be divided into a plurality of groups, each of which is formed of 16 adjacent pixels Pi (16 pixels Pi including four pixels Pi in each of the columns and including four pixels Pi in each of the rows). In this state, the R, G, and B filters 542R, 542G, and 542B are arranged in a Bayer array, when the 16 pixels Pi included in a group have the same filter and the group (16 pixels Pi) is regarded as one pixel, as illustrated in FIG. 16.

In the case of the structure described above, in the normal mode, the exposure time of all the pixels of the imaging element 541 is set to the equal time. The imaging unit 54 outputs each of the pixel signals output from the respective pixels Pi, as pixel signal of one pixel.

In the HDR mode, in all the pixels of the imaging element 541, the exposure time of at least one of 16 pixels Pi included in each one of the groups is set to have an exposure time different from the exposure time of the other pixels Pi. The imaging unit 54 outputs, for each of the groups, an addition pixel signal obtained by adding the pixel signals of the 16 pixels included in the group, as a pixel signal of one pixel.

In the high-sensitivity mode, the exposure time of all the pixels of the imaging element 541 is set to the equal time. The imaging unit 54 outputs, for each of the groups, an addition pixel signal obtained by adding the pixel signals of the 16 pixels included in the group, as a pixel signal of one pixel Pi.

Figure 17:
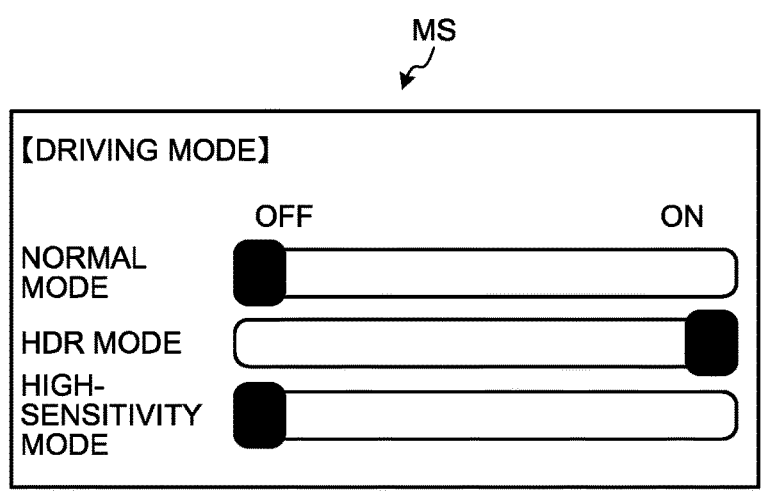
FIG. 17 is a diagram illustrating a third modification of the first to the fifth embodiments.

FIG. 17 is a diagram illustrating a third modification of the first to the fifth embodiments.

The first to the fifth embodiments described above have the structure in which the driving mode of the imaging unit 54 is automatically set to one of the normal mode, the HDR mode, and the high-sensitivity mode, but the structure is not limited thereto. The mode may be set in accordance with a user's operation input or user's voice. For example, a structure as illustrated in FIG. 17 may be adopted. As illustrated in FIG. 17, the user selects one of the normal mode, the HDR mode, and the high-sensitivity mode, by a user's operation on the input unit 95 on the menu picture MS displayed on the display device 7, or an operation on the operating unit (not illustrated) provided on the camera head 5.

Figure 18:
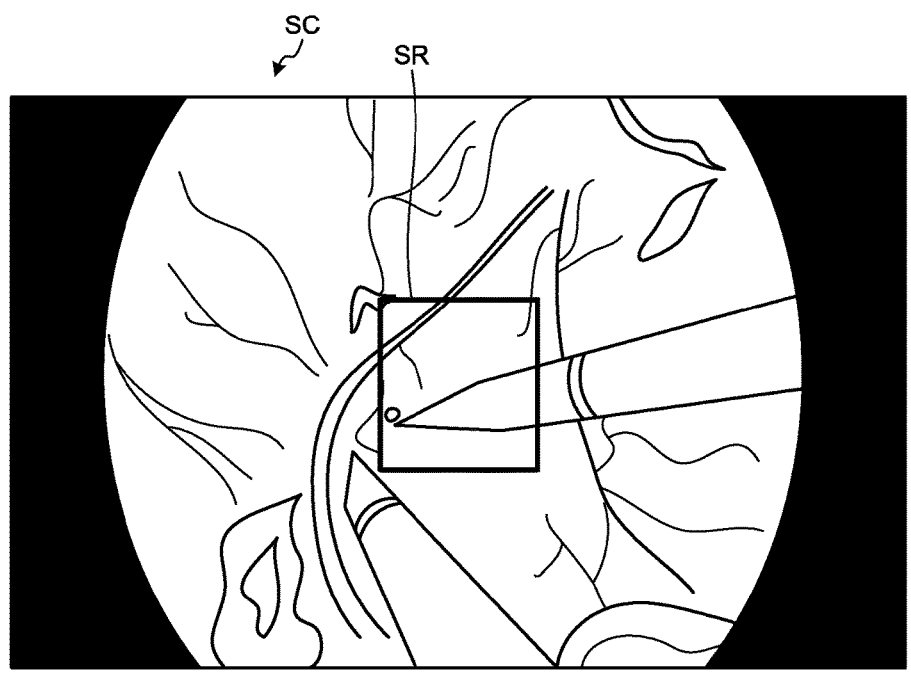
FIG. 18 is a diagram illustrating a fourth modification of the first to the fifth embodiments.

FIG. 18 is a diagram illustrating a fourth modification of the first to the fifth embodiments.

The first to the fifth embodiments described above have the structure in which all the pixels of the imaging element 541 are driven in one of the normal mode, the HDR mode, and the high-sensitivity mode, but the structure is not limited thereto. Only a range designated in accordance with a user's operation input or user's voice may be driven in one of the driving modes. For example, as illustrated in FIG. 18, on a display screen SC of the display device 7, only pixels in a selected range SR selected by a user's operation on the input unit 95 or the operating unit (not illustrated) provided on the camera head 5 may be driven in one of the driving modes. The pixels outside the selected range SR are driven, for example, in the normal mode. The Y gamma correction unit 9231 performs Y gamma correction only on the luminance signals (Y signals) corresponding to the pixels in the selected range SR, in the luminance signals (Y signals) included in the image signal (Y, $C_B/C_R$ signals) having been subjected to RGB processing in the RGB processor 922, with the Y gamma curve corresponding to the driving mode.

The first to the fifth embodiments described above have the structure in which a histogram of the luminance signal (Y signal) is calculated, and the imaging unit 54 is set to one driving mode of the normal mode, the HDR mode, and the high-sensitivity mode based on the histogram, but the structure is not limited thereto. For example, the brightness of the whole image imaged with the imaging unit 54 may be determined, and the imaging unit 54 may be set to one driving mode of the normal mode, the HDR mode, and the high-sensitivity mode, in accordance with the determination result.

The first to the fifth embodiments described above are provided with three driving modes of the normal mode, the HDR mode, and the high-sensitivity mode, as the driving modes of the imaging unit 54, but the structure is not limited thereto. A structure may be adopted to include only two driving modes in the three driving modes.

The first to the fifth embodiments described above may adopt a structure in which the first to the third thresholds Th1 to Th3 may be changed manually or automatically. For example, because the number of all the pixels in calculation of a histogram differs (the number of pixels in the case of the HDR mode or the high-sensitivity mode is smaller than the number of pixels in the case of the normal mode) between the case in which the current driving mode of the imaging unit 54 is the normal mode and the case in which the current driving mode is the HDR mode or the high-sensitivity mode, the embodiments may adopt a structure in which the first threshold Th1 is automatically changed to a lower threshold than the first threshold in the normal mode, when the current driving mode of the imaging unit 54 is the HDR mode or the high-sensitivity mode.

The first to the fifth embodiments described above may have a structure in which the signal processor 92, 92A, or 92B, the mode setting unit 941, and the imaging controller 942 are provided outside the controller 9, 9A, or 9B. For example, the signal processor 92, 92A, or 92B, the mode setting unit 941, and the imaging controller 942 may be provided on the camera head 5, the connectors CN1 and CN2, the endoscope 11, or the surgical microscope 12.

The first to the fifth embodiments described above may have a structure in which the mode setting unit 941 is configured to perform dimming control of the light source device 3, in accordance with the driving mode set with the mode setting unit 941.

In the first to the fifth embodiments described above and the first and the second modifications described above, the relation of the exposure time of the pixels included in a group in the HDR mode is not limited to the relations explained in the first to the fifth embodiments described above and the first and the second modifications described above. As long as at least one of all the pixels included in each one of the groups is set to have an exposure time different from the exposure time of the other pixels, for example, all the pixels may be set to different exposure times.

The third to fifth embodiments described above may adopt a structure in which the Y gamma correction unit 9231 or 9231B, in the same manner as the second embodiment described above.

The medical imaging apparatus according to the present disclosure includes a mode setting unit setting the driving mode of the imaging unit to one of at least two driving modes of first to third driving modes.

The first driving mode is a driving mode of setting the exposure time of all the pixels in the imaging unit to equal time, and outputting a pixel signal of each of all the pixels as a pixel signal of one pixel. Specifically, the first driving mode is a normal mode that normally drives the imaging unit.

The second driving mode is a driving mode that divides all the pixels into a plurality of groups, each of which is formed of adjacent pixels in all the pixels in the imaging unit, setting at least one of the pixels included in each one of the groups to have an exposure time different from the exposure time of the other pixels, and outputting, for each of the groups, an addition pixel signal obtained by adding pixel signals of all the pixels included in the group, as pixel signal of one pixel. Specifically, the second driving mode is a high dynamic range (HDR) mode capable of increasing the sensitivity in the case of a low incident light quantity, decreasing the sensitivity in the case of a high incident light quantity, and achieving a wide dynamic range, by adding pixel signals of the respective pixels included in a group and having different exposure times.

In addition, the third driving mode is a driving mode that sets the exposure time of all the pixels in the imaging unit to an equal time, and outputs, for each of the groups, an addition pixel signal obtained by adding pixel signals of all the pixels included in the group, as pixel signal of one pixel. Specifically, the third driving mode is a high-sensitivity mode capable of increasing the sensitivity in the case of a low incident light quantity, by adding the pixel signals of the respective pixels included in a group and having the equal exposure time to increase the signal level per pixel (addition pixel signal).

For example, when an image suitable for observation is displayed, the driving mode of the imaging unit is set to the first driving mode (normal mode). However, when an image (an image in which bright portions form blown-out highlights, an image in which dark portions form blocked-up shadows, or an image in which a forceps or white gauze enters the subject and the whole image is brightened) unsuitable for observation is displayed, the driving mode of the imaging unit is set to the second driving mode (HDR mode) or the third driving mode (high-sensitivity mode). Setting the driving mode of the imaging unit as described above enables display of an image suitable for observation, and improves convenience.

Accordingly, the medical imaging apparatus according to the present disclosure produces the effects of removing the necessity for providing a plurality of imaging elements having different sensitivities, and enabling improvement in convenience without complicating the structure.

In addition, the medical observation system according to the prevent disclosure includes the medical imaging apparatus as described above, and produces the functions and effects similar to those of the medical imaging apparatus described above.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging apparatus comprising: an imager including a plurality of pixels arranged in a matrix;
   a mode setting circuitry configured to set a driving mode of the imager from a plurality of driving modes including a first driving mode and a second driving mode;
   and an imaging controller configured to drive the imager in accordance with the driving mode set with the mode setting circuitry, wherein the first driving mode is a driving mode that sets exposure time of all the pixels in the imager to an equal time, the second driving mode is a driving mode that divides all the pixels into a plurality of groups, each of which is formed of a plurality of adjacent pixels in all the pixels, setting at least one of all the pixels included in the group to have an exposure time different from an exposure time of the other pixels.

2. The medical imaging apparatus according to claim 1, wherein the mode setting circuitry sets the driving mode of the imager from a plurality of driving modes based on brightness of an image imaged with the imager.

3. The medical imaging apparatus according to claim 2, further comprising:
   a histogram calculator configured to calculate a histogram of a luminance signal for each of pixels in the image imaged with the imager, wherein the mode setting circuitry sets the driving mode of the imager from a plurality of driving modes based on the histogram calculated with the histogram calculator.

4. The medical imaging apparatus according to claim 2, wherein the plurality of driving modes further including a third driving mode;
   and the third driving mode is a driving mode that sets exposure time of all the pixels to an equal time, and outputs, for each of the groups, an addition pixel signal obtained by adding pixel signals of all the pixels in the group, as a pixel signal of one pixel.

5. The medical imaging apparatus according to claim 4, further comprising: a Y gamma correction circuitry performing Y gamma correction on a luminance signal for each of pixels in an image imaged with the imager, wherein a Y gamma curve in the Y gamma correction differs among a case in which the driving mode of the imager is set to the first driving mode, a case in which the driving mode is set to the second driving mode, and a case in which the driving mode is set to the third driving mode.

6. The medical imaging apparatus according to claim 5, wherein the imager images a subject image captured with an endoscope inserted into a subject, the image imaged with the imager includes the subject image and a mask area other than the subject image,
   the medical imaging apparatus further comprises an edge detection circuitry configured to detect boundary points between the subject image and the mask area based on the luminance signal for each of the pixels in the image imaged with the imager, and the Y gamma correction circuitry performs the Y gamma correction only on an area enclosed with the boundary points detected with the edge detection unit in the whole image imaged with the imager.

7. The medical imaging apparatus according to claim 5, wherein the imager includes: a color filter in which three filters divided into groups in accordance with wavelength bands of R, G, and B are arranged in a predetermined form;
   and an imaging element including a light receiving surface provided with the color filter;

and the three filters are arranged such that all the pixels included in the group have a same filter, and the groups are provided with different filters.

8. A medical observation system comprising: the medical imaging apparatus according to claim 5; and a display device displaying an image imaged with the medical imaging apparatus.

* * * * *